(12) United States Patent
Emery et al.

(10) Patent No.: US 11,399,744 B2
(45) Date of Patent: Aug. 2, 2022

(54) DETECTION METER AND MODE OF OPERATION

(71) Applicant: Intuity Medical, Inc., Sunnyvale, CA (US)

(72) Inventors: Jeffrey L. Emery, Redwood City, CA (US); Michael F. Tomasco, Morgan Hill, CA (US); Charles Hu, Palo Alto, CA (US)

(73) Assignee: Intuity Medical, Inc., Sunnyvale, CA (US)

( * ) Notice: Subject to any disclaimer, the term of this patent is extended or adjusted under 35 U.S.C. 154(b) by 0 days.

(21) Appl. No.: 15/499,821

(22) Filed: Apr. 27, 2017

(65) Prior Publication Data

US 2017/0354355 A1 Dec. 14, 2017

Related U.S. Application Data

(63) Continuation of application No. 12/457,331, filed on Jun. 8, 2009, now Pat. No. 9,636,051.
(Continued)

(51) Int. Cl.
*A61B 5/145* (2006.01)
*A61B 5/15* (2006.01)
(Continued)

(52) U.S. Cl.
CPC .......... *A61B 5/14532* (2013.01); *A61B 5/157* (2013.01); *A61B 5/150022* (2013.01);
(Continued)

(58) Field of Classification Search
CPC ........ A61B 5/150022; A61B 5/150099; A61B 5/15109; A61B 5/157; A61B 5/150068;
(Continued)

(56) References Cited

U.S. PATENT DOCUMENTS

| 842,690 A | 1/1907 | Oswalt |
| D137,874 S | 5/1944 | Partridge |

(Continued)

FOREIGN PATENT DOCUMENTS

| CA | 2 513 465 A1 | 8/2004 |
| DE | 199 22 413 A1 | 11/2000 |

(Continued)

OTHER PUBLICATIONS

ADA Consensus Development Panel. (Jan.-Feb. 1987). "Consensus Statement on Self-Monitoring of Blood Glucose," *Diabetes Care* 10(1):95-99.
(Continued)

*Primary Examiner* — Samuel P Siefke
(74) *Attorney, Agent, or Firm* — Cooley LLP

(57) ABSTRACT

A method for performing an assay to determine the presence or concentration of an analyte contained in a sample of body fluid by using a device comprising at least one analyte quantification member and a sensor associated therewith, the method includes: applying a first sample to the analyte quantification member; and detecting the presence or absence of an adequate sample volume; wherein upon detection of the absence of an adequate sample volume, initiating a finite timed period, and signaling the user to introduce a second sample of body fluid to the analyte quantification member. Associated arrangements and devices are also disclosed.

28 Claims, 6 Drawing Sheets

Related U.S. Application Data

(60) Provisional application No. 61/129,149, filed on Jun. 6, 2008.

(51) Int. Cl.
*A61B 5/151* (2006.01)
*A61B 5/157* (2006.01)
*A61B 5/1455* (2006.01)
*A61B 5/1468* (2006.01)

(52) U.S. Cl.
CPC .... *A61B 5/150099* (2013.01); *A61B 5/15109* (2013.01); *A61B 5/15113* (2013.01); *A61B 5/15163* (2013.01); *A61B 5/150358* (2013.01); *A61B 5/150396* (2013.01); *A61B 5/150503* (2013.01); *A61B 5/150755* (2013.01); *A61B 5/150809* (2013.01); *A61B 5/150824* (2013.01); *A61B 5/150954* (2013.01); *A61B 5/1455* (2013.01); *A61B 5/1468* (2013.01); *A61B 2560/0276* (2013.01); *A61B 2562/0295* (2013.01)

(58) Field of Classification Search
CPC ........ A61B 5/150358; A61B 5/150389; A61B 5/150503; A61B 5/150748; A61B 5/15113; A61B 5/15117; A61B 5/15151; A61B 5/15161; A61B 5/1411; A61B 5/150809; A61B 5/150824; A61B 5/150954; A61B 5/15123; A61B 5/15125; A61B 2560/0276; A61B 2562/0295; A61B 5/14532; A61B 5/1455; A61B 5/1468; A61B 5/150076; A61B 5/150083; A61B 5/150091; A61B 5/150183; A61B 5/150229; A61B 5/150259; A61B 5/150267; A61B 5/150274; A61B 5/150396; A61B 5/150412; A61B 5/150442; A61B 5/150755; A61B 5/150816; A61B 5/150832; A61B 5/150984; A61B 5/15107; A61B 5/15163; A61M 5/422

See application file for complete search history.

(56) References Cited

U.S. PATENT DOCUMENTS

| | | |
|---|---|---|
| 2,749,797 A | 3/1950 | Harks |
| 3,092,465 A | 6/1963 | Adams, Jr. |
| 3,310,002 A | 3/1967 | Wilburn |
| 3,620,209 A | 11/1971 | Kravitz |
| 3,623,475 A | 11/1971 | Sanz et al. |
| 3,626,929 A | 12/1971 | Sanz et al. |
| 3,630,957 A | 12/1971 | Rey |
| D223,165 S | 3/1972 | Komendat |
| 3,723,064 A | 3/1973 | Liotta |
| 3,741,197 A | 6/1973 | Sanz et al. |
| 3,961,898 A | 6/1976 | Neeley et al. |
| 3,992,158 A | 11/1976 | Przybylowicz et al. |
| 4,014,328 A | 3/1977 | Cluff et al. |
| 4,042,335 A | 8/1977 | Clement |
| 4,057,394 A | 11/1977 | Genshaw |
| 4,109,655 A | 8/1978 | Chacornac |
| 4,250,257 A | 2/1981 | Lee et al. |
| 4,253,083 A | 2/1981 | Imamura |
| 4,254,083 A | 3/1981 | Columbus |
| 4,258,001 A | 3/1981 | Pierce et al. |
| 4,260,257 A | 4/1981 | Neeley et al. |
| 4,289,459 A | 9/1981 | Neeley et al. |
| 4,321,397 A | 3/1982 | Nix et al. |
| 4,350,762 A | 9/1982 | DeLuca et al. |
| 4,394,512 A | 7/1983 | Batz |
| 4,414,975 A | 11/1983 | Ryder et al. |
| 4,416,279 A | 11/1983 | Lindner et al. |
| 4,418,037 A | 11/1983 | Katsuyama et al. |
| 4,422,941 A | 12/1983 | Vaughan, Jr. et al. |
| 4,429,700 A | 2/1984 | Thees et al. |
| 4,627,445 A | 12/1986 | Garcia et al. |
| 4,637,403 A | 1/1987 | Garcia et al. |
| 4,637,406 A | 1/1987 | Guinn et al. |
| 4,653,513 A | 3/1987 | Dombrowski |
| 4,661,319 A | 4/1987 | Lape |
| 4,702,261 A | 10/1987 | Cornell et al. |
| 4,711,250 A | 12/1987 | Gilbaugh, Jr. et al. |
| 4,737,458 A | 4/1988 | Batz et al. |
| 4,747,687 A | 5/1988 | Hoppe et al. |
| 4,767,415 A | 8/1988 | Duffy |
| 4,774,192 A | 9/1988 | Terminiello et al. |
| 4,787,398 A | 11/1988 | Garcia et al. |
| 4,790,979 A | 12/1988 | Terminiello et al. |
| 4,794,926 A | 1/1989 | Munsch et al. |
| 4,815,843 A | 3/1989 | Tiefenthaler et al. |
| 4,829,470 A | 5/1989 | Wang |
| 4,844,095 A | 7/1989 | Chiodo et al. |
| 4,846,785 A | 7/1989 | Cassou et al. |
| 4,887,306 A | 12/1989 | Hwang et al. |
| 4,920,977 A | 5/1990 | Haynes |
| 4,929,426 A | 5/1990 | Bodai et al. |
| 4,930,525 A | 6/1990 | Palestrant |
| 4,935,346 A | 6/1990 | Phillips |
| 4,953,552 A | 9/1990 | De Marzo |
| 4,966,646 A | 10/1990 | Zdeblick |
| 4,983,178 A | 1/1991 | Schnell |
| 4,995,402 A | 2/1991 | Smith |
| 5,029,583 A | 7/1991 | Meserol |
| 5,035,704 A | 7/1991 | Lambert et al. |
| 5,037,199 A | 8/1991 | Hlousek |
| 5,049,487 A | 9/1991 | Phillips et al. |
| 5,050,617 A | 9/1991 | Columbus et al. |
| 5,054,878 A | 10/1991 | Gergely et al. |
| 5,059,394 A | 10/1991 | Phillips et al. |
| 5,077,199 A | 12/1991 | Basagni et al. |
| 5,094,943 A | 3/1992 | Siedel et al. |
| 5,110,724 A | 5/1992 | Hewett |
| 5,114,350 A | 5/1992 | Hewett |
| 5,116,759 A | 5/1992 | Klainer et al. |
| 5,131,404 A | 7/1992 | Neeley et al. |
| 5,141,868 A | 8/1992 | Shanks et al. |
| 5,145,565 A | 9/1992 | Kater et al. |
| 5,146,437 A | 9/1992 | Boucheron |
| 5,153,416 A | 10/1992 | Neeley |
| 5,164,575 A | 11/1992 | Neeley et al. |
| 5,166,498 A | 11/1992 | Neeley |
| 5,174,291 A | 12/1992 | Schoonen et al. |
| 5,176,632 A | 1/1993 | Bernardi |
| 5,179,005 A | 1/1993 | Phillips et al. |
| 5,183,741 A | 2/1993 | Arai et al. |
| 5,194,393 A | 3/1993 | Hugl et al. |
| 5,196,302 A | 3/1993 | Kidwell |
| 5,208,163 A | 5/1993 | Charlton et al. |
| 5,213,966 A | 5/1993 | Vuorinen et al. |
| 5,217,480 A | 6/1993 | Habar et al. |
| 5,218,966 A | 6/1993 | Yamasawa |
| 5,223,219 A | 6/1993 | Subramanian et al. |
| 5,228,972 A | 7/1993 | Osaka et al. |
| 5,234,818 A | 8/1993 | Zimmermann et al. |
| 5,241,969 A | 9/1993 | Carson et al. |
| 5,251,126 A | 10/1993 | Kahn et al. |
| D341,848 S | 11/1993 | Bigelow et al. |
| 5,269,800 A | 12/1993 | Davis, Jr. |
| 5,275,159 A | 1/1994 | Griebel |
| 5,278,079 A | 1/1994 | Gubinski et al. |
| 5,279,294 A | 1/1994 | Anderson et al. |
| 5,288,646 A | 2/1994 | Lundsgaard et al. |
| 5,299,571 A | 4/1994 | Mastrototaro |
| 5,301,686 A | 4/1994 | Newman |
| 5,302,513 A | 4/1994 | Mike et al. |
| 5,304,468 A | 4/1994 | Phillips et al. |
| 5,306,623 A | 4/1994 | Kiser et al. |
| 5,308,767 A | 5/1994 | Terashima |
| 5,314,441 A | 5/1994 | Cusack et al. |
| 5,320,607 A | 6/1994 | Ishibashi |

(56) References Cited

U.S. PATENT DOCUMENTS

| | | |
|---|---|---|
| 5,354,537 A | 10/1994 | Moreno |
| 5,360,595 A | 11/1994 | Bell et al. |
| 5,368,047 A | 11/1994 | Suzuki et al. |
| 5,383,512 A | 1/1995 | Jarvis |
| 5,390,671 A | 2/1995 | Lord et al. |
| 5,395,388 A | 3/1995 | Schraga |
| 5,399,316 A | 3/1995 | Yamada |
| 5,401,110 A | 3/1995 | Neeley |
| 5,402,798 A | 4/1995 | Swierczek et al. |
| 5,426,032 A | 6/1995 | Phillips et al. |
| 5,441,513 A | 8/1995 | Roth |
| 5,451,350 A | 9/1995 | Macho et al. |
| 5,458,140 A | 10/1995 | Eppstein et al. |
| 5,460,777 A | 10/1995 | Kitajima et al. |
| 5,460,968 A | 10/1995 | Yoshida et al. |
| 5,482,473 A | 1/1996 | Lord et al. |
| 5,489,414 A | 2/1996 | Schreiber et al. |
| 5,506,200 A | 4/1996 | Hirschkoff et al. |
| 5,507,288 A | 4/1996 | Böcker et al. |
| 5,508,200 A | 4/1996 | Tiffany et al. |
| 5,510,266 A | 4/1996 | Bonner et al. |
| 5,514,152 A | 5/1996 | Smith |
| 5,518,689 A | 5/1996 | Dosmann et al. |
| 5,525,518 A | 6/1996 | Lundsgaard et al. |
| 5,527,892 A | 6/1996 | Borsotti et al. |
| 5,563,042 A | 10/1996 | Phillips et al. |
| 5,568,806 A | 10/1996 | Cheney, II et al. |
| 5,569,287 A | 10/1996 | Tezuka et al. |
| 5,575,403 A | 11/1996 | Charlton et al. |
| 5,577,499 A | 11/1996 | Teves |
| 5,582,184 A | 12/1996 | Erickson et al. |
| 5,586,553 A | 12/1996 | Halili et al. |
| 5,591,139 A | 1/1997 | Lin et al. |
| 5,593,838 A | 1/1997 | Zanzucchi et al. |
| 5,602,647 A | 2/1997 | Xu et al. |
| 5,611,809 A | 3/1997 | Marshall et al. |
| 5,611,999 A | 3/1997 | Dosmann et al. |
| 5,624,458 A | 4/1997 | Lipscher |
| 5,630,986 A | 5/1997 | Charlton et al. |
| 5,632,410 A | 5/1997 | Moulton et al. |
| 5,636,632 A | 6/1997 | Bommannan et al. |
| 5,638,828 A | 6/1997 | Lauks et al. |
| 5,647,851 A | 7/1997 | Pokras |
| 5,658,515 A | 8/1997 | Lee et al. |
| 5,660,791 A | 8/1997 | Brenneman et al. |
| 5,670,031 A | 9/1997 | Hintsche et al. |
| 5,676,850 A | 10/1997 | Reed et al. |
| 5,680,858 A | 10/1997 | Hansen et al. |
| 5,681,484 A | 10/1997 | Zanzucchi et al. |
| 5,682,233 A | 10/1997 | Brinda |
| 5,697,901 A | 12/1997 | Eriksson |
| 5,701,181 A | 12/1997 | Boiarski et al. |
| 5,701,910 A | 12/1997 | Powles et al. |
| D389,761 S | 1/1998 | Thomas |
| 5,705,018 A | 1/1998 | Hartley |
| 5,708,247 A | 1/1998 | McAleer |
| 5,708,787 A | 1/1998 | Nakano et al. |
| 5,715,417 A | 2/1998 | Gardien et al. |
| 5,730,753 A | 3/1998 | Morita |
| 5,735,273 A | 4/1998 | Kurnik et al. |
| 5,736,103 A | 4/1998 | Pugh |
| 5,741,211 A | 4/1998 | Renirie et al. |
| 5,746,217 A | 5/1998 | Erickson et al. |
| 5,746,720 A | 5/1998 | Stouder, Jr. |
| 5,753,452 A | 5/1998 | Smith |
| 5,757,666 A | 5/1998 | Schreiber et al. |
| 5,759,364 A | 6/1998 | Charlton et al. |
| 5,766,066 A | 6/1998 | Ranniger |
| 5,771,890 A | 6/1998 | Tamada |
| 5,789,255 A | 8/1998 | Yu |
| 5,797,693 A | 8/1998 | Jaeger |
| 5,800,420 A | 9/1998 | Gross et al. |
| 5,801,057 A | 9/1998 | Smart et al. |
| 5,807,375 A | 9/1998 | Gross et al. |
| 5,820,570 A | 10/1998 | Erickson et al. |
| 5,827,183 A | 10/1998 | Kurnik et al. |
| 5,840,020 A | 11/1998 | Heinonen et al. |
| 5,841,126 A | 11/1998 | Fossum et al. |
| 5,843,692 A | 12/1998 | Phillips et al. |
| 5,846,837 A | 12/1998 | Thym et al. |
| 5,851,215 A | 12/1998 | Mawhirt et al. |
| 5,854,074 A | 12/1998 | Charlton et al. |
| D403,975 S | 1/1999 | Douglas et al. |
| 5,855,801 A | 1/1999 | Lin et al. |
| 5,856,195 A | 1/1999 | Charlton et al. |
| 5,858,194 A | 1/1999 | Bell |
| 5,866,281 A | 2/1999 | Guckel et al. |
| 5,866,349 A | 2/1999 | Lilja et al. |
| 5,871,494 A | 2/1999 | Simons et al. |
| 5,879,310 A | 3/1999 | Sopp et al. |
| 5,879,326 A | 3/1999 | Godshall et al. |
| 5,879,367 A | 3/1999 | Latterell et al. |
| 5,885,839 A | 3/1999 | Lingane et al. |
| 5,891,053 A | 4/1999 | Sesekura |
| 5,893,870 A | 4/1999 | Talen et al. |
| D411,621 S | 6/1999 | Eisenbarth et al. |
| 5,911,711 A | 6/1999 | Pelkey |
| 5,911,737 A | 6/1999 | Lee et al. |
| 5,912,139 A | 6/1999 | Iwata et al. |
| 5,925,021 A | 7/1999 | Castellano et al. |
| 5,926,271 A | 7/1999 | Couderc et al. |
| 5,928,207 A | 7/1999 | Pisano et al. |
| 5,930,873 A | 8/1999 | Wyser |
| 5,938,679 A | 8/1999 | Freeman et al. |
| 5,945,678 A | 8/1999 | Yanagisawa |
| 5,951,492 A | 9/1999 | Douglas et al. |
| 5,951,493 A | 9/1999 | Douglas et al. |
| 5,951,521 A | 9/1999 | Mastrototaro et al. |
| 5,954,685 A | 9/1999 | Tierney |
| 5,962,215 A | 10/1999 | Douglas et al. |
| 5,968,760 A | 10/1999 | Phillips et al. |
| 5,968,765 A | 10/1999 | Grage et al. |
| 5,968,836 A | 10/1999 | Matzinger et al. |
| 5,971,941 A | 10/1999 | Simons et al. |
| 5,972,294 A | 10/1999 | Smith et al. |
| 5,986,754 A | 11/1999 | Harding |
| 5,989,409 A | 11/1999 | Kurnik et al. |
| 5,993,189 A | 11/1999 | Mueller et al. |
| D417,504 S | 12/1999 | Love et al. |
| 6,001,067 A | 12/1999 | Shults et al. |
| 6,005,545 A | 12/1999 | Nishida et al. |
| 6,010,463 A | 1/2000 | Lauks et al. |
| 6,010,519 A | 1/2000 | Mawhirt et al. |
| 6,014,135 A | 1/2000 | Fernandes |
| 6,014,577 A | 1/2000 | Henning et al. |
| 6,015,969 A | 1/2000 | Nathel et al. |
| 6,023,629 A | 2/2000 | Tamada |
| 6,027,459 A | 2/2000 | Shain et al. |
| 6,030,827 A | 2/2000 | Davis et al. |
| 6,032,059 A | 2/2000 | Henning et al. |
| 6,036,924 A | 3/2000 | Simons et al. |
| 6,041,253 A | 3/2000 | Kost et al. |
| 6,045,753 A | 4/2000 | Loewy et al. |
| 6,048,352 A | 4/2000 | Douglas et al. |
| 6,050,988 A | 4/2000 | Zuck |
| 6,056,701 A | 5/2000 | Duchon et al. |
| 6,056,734 A | 5/2000 | Jacobsen et al. |
| 6,058,321 A | 5/2000 | Swayze et al. |
| 6,059,815 A | 5/2000 | Lee et al. |
| 6,061,128 A | 5/2000 | Zweig et al. |
| 6,063,039 A | 5/2000 | Cunningham et al. |
| 6,071,251 A | 6/2000 | Cunningham et al. |
| 6,071,294 A | 6/2000 | Simons et al. |
| 6,077,660 A | 6/2000 | Wong et al. |
| 6,080,116 A | 6/2000 | Erickson et al. |
| 6,083,196 A | 7/2000 | Trautman et al. |
| 6,086,544 A | 7/2000 | Hibner et al. |
| 6,090,790 A | 7/2000 | Eriksson |
| 6,091,975 A | 7/2000 | Daddona et al. |
| 6,093,156 A | 7/2000 | Cunningham et al. |
| 6,097,831 A | 8/2000 | Wieck et al. |
| 6,099,484 A | 8/2000 | Douglas et al. |
| 6,100,107 A | 8/2000 | Lei et al. |
| 6,102,933 A | 8/2000 | Lee et al. |

(56) References Cited

U.S. PATENT DOCUMENTS

| | | |
|---|---|---|
| 6,103,033 A | 8/2000 | Say et al. |
| 6,103,197 A | 8/2000 | Werner |
| 6,106,751 A | 8/2000 | Talbot et al. |
| 6,118,126 A | 9/2000 | Zanzucchi |
| 6,120,676 A | 9/2000 | Heller et al. |
| 6,121,050 A | 9/2000 | Han |
| 6,123,861 A | 9/2000 | Santini, Jr. et al. |
| 6,126,899 A | 10/2000 | Woudenberg et al. |
| 6,132,449 A | 10/2000 | Lum et al. |
| 6,139,562 A | 10/2000 | Mauze et al. |
| 6,142,939 A | 11/2000 | Eppstein et al. |
| 6,152,942 A | 11/2000 | Brenneman et al. |
| 6,162,639 A | 12/2000 | Douglas |
| 6,172,743 B1 | 1/2001 | Kley et al. |
| 6,175,752 B1 | 1/2001 | Say et al. |
| 6,176,865 B1 | 1/2001 | Mauze et al. |
| 6,183,434 B1 | 2/2001 | Eppstein et al. |
| 6,183,489 B1 | 2/2001 | Douglas et al. |
| 6,184,990 B1 | 2/2001 | Amirkhanian et al. |
| 6,187,210 B1 | 2/2001 | Lebouiz et al. |
| 6,192,891 B1 | 2/2001 | Gravel et al. |
| 6,193,873 B1 | 2/2001 | Ohara et al. |
| 6,197,257 B1 | 3/2001 | Raskas |
| 6,200,296 B1 | 3/2001 | Dibiasi et al. |
| 6,206,841 B1 | 3/2001 | Cunningham et al. |
| 6,214,626 B1 | 4/2001 | Meller et al. |
| 6,219,574 B1 | 4/2001 | Cormier et al. |
| 6,228,100 B1 | 5/2001 | Schraga |
| 6,230,051 B1 | 5/2001 | Cormier et al. |
| 6,231,531 B1 | 5/2001 | Lum et al. |
| 6,241,862 B1 | 6/2001 | McAleer et al. |
| 6,242,207 B1 | 6/2001 | Douglas et al. |
| 6,245,215 B1 | 6/2001 | Douglas et al. |
| 6,246,966 B1 | 6/2001 | Perry |
| 6,251,083 B1 | 6/2001 | Yum et al. |
| 6,251,260 B1 | 6/2001 | Heller et al. |
| 6,254,586 B1 | 7/2001 | Mann et al. |
| 6,255,061 B1 | 7/2001 | Mori et al. |
| 6,256,533 B1 | 7/2001 | Yuzhakov et al. |
| 6,268,162 B1 | 7/2001 | Phillips et al. |
| 6,271,045 B1 | 8/2001 | Douglas et al. |
| 6,272,364 B1 | 8/2001 | Kurnik |
| 6,283,926 B1 | 9/2001 | Cunningham et al. |
| 6,289,230 B1 | 9/2001 | Chaiken et al. |
| 6,298,254 B2 | 10/2001 | Tamada |
| 6,299,578 B1 | 10/2001 | Kurnik et al. |
| 6,299,757 B1 | 10/2001 | Feldman et al. |
| 6,306,104 B1 | 10/2001 | Cunningham et al. |
| 6,309,351 B1 | 10/2001 | Kurnik et al. |
| D450,711 S | 11/2001 | Istvan et al. |
| 6,312,612 B1 | 11/2001 | Sherman et al. |
| 6,312,888 B1 | 11/2001 | Wong et al. |
| 6,315,738 B1 | 11/2001 | Nishikawa et al. |
| 6,322,808 B1 | 11/2001 | Trautman et al. |
| 6,329,161 B1 | 12/2001 | Heller et al. |
| 6,331,266 B1 | 12/2001 | Powell et al. |
| 6,332,871 B1 | 12/2001 | Douglas et al. |
| 6,334,856 B1 | 1/2002 | Allen et al. |
| 6,350,273 B1 | 2/2002 | Minagawa et al. |
| 6,352,514 B1 | 3/2002 | Douglas et al. |
| 6,356,776 B1 | 3/2002 | Berner et al. |
| 6,358,265 B1 | 3/2002 | Thorne, Jr. et al. |
| 6,364,890 B1 | 4/2002 | Lum et al. |
| 6,375,626 B1 | 4/2002 | Allen et al. |
| 6,375,627 B1 | 4/2002 | Mauze et al. |
| 6,379,969 B1 | 4/2002 | Mauze et al. |
| 6,391,005 B1 | 5/2002 | Lum et al. |
| 6,391,645 B1 | 5/2002 | Huang et al. |
| 6,402,704 B1 | 6/2002 | McMorrow |
| 6,409,679 B2 | 6/2002 | Pyo |
| 6,428,664 B1 | 8/2002 | BhulLar et al. |
| 6,449,608 B1 | 9/2002 | Morita et al. |
| 6,455,324 B1 | 9/2002 | Douglas |
| 6,493,069 B1 | 12/2002 | Nagashimada et al. |
| 6,500,134 B1 | 12/2002 | Cassone |
| 6,520,973 B1 | 2/2003 | McGarry |
| 6,530,892 B1 | 3/2003 | Kelly |
| 6,537,243 B1 | 3/2003 | Henning et al. |
| 6,540,675 B2 | 4/2003 | Aceti et al. |
| 6,544,193 B2 | 4/2003 | Abreu |
| 6,544,475 B1 | 4/2003 | Douglas et al. |
| 6,549,796 B2 | 4/2003 | Sohrab |
| 6,555,061 B1 | 4/2003 | Leong et al. |
| 6,558,624 B1 | 5/2003 | Lemmon et al. |
| 6,579,690 B1 | 6/2003 | Bonnecaze et al. |
| 6,589,260 B1 | 7/2003 | Schmelzeisen-Redeker et al. |
| 6,591,124 B2 | 7/2003 | Sherman et al. |
| 6,591,125 B1 | 7/2003 | Buse et al. |
| 6,602,205 B1 | 8/2003 | Erickson et al. |
| 6,612,111 B1 | 9/2003 | Hodges et al. |
| 6,616,616 B2 | 9/2003 | Fritz et al. |
| 6,626,874 B1 | 9/2003 | Duchamp |
| 6,656,167 B2 | 12/2003 | Numao et al. |
| 6,662,031 B1 | 12/2003 | Khalil et al. |
| 6,679,852 B1 | 1/2004 | Schmelzeisen-Redeker et al. |
| 6,690,467 B1 | 2/2004 | Reel |
| 6,706,000 B2 | 3/2004 | Perez et al. |
| 6,706,049 B2 | 3/2004 | Moerman |
| 6,706,159 B2 | 3/2004 | Moerman et al. |
| 6,707,554 B1 | 3/2004 | Miltner et al. |
| 6,740,800 B1 | 5/2004 | Cunningham |
| 6,743,635 B2 | 6/2004 | Neel et al. |
| 6,744,502 B2 | 6/2004 | Hoff et al. |
| 6,748,275 B2 | 6/2004 | Lattner et al. |
| 6,753,187 B2 | 6/2004 | Cizdziel et al. |
| 6,766,817 B2 | 7/2004 | da Silva |
| 6,775,001 B2 | 8/2004 | Friberg et al. |
| 6,793,633 B2 | 9/2004 | Douglas et al. |
| 6,830,669 B2 | 12/2004 | Miyazaki et al. |
| 6,836,678 B2 | 12/2004 | Tu |
| 6,837,858 B2 | 1/2005 | Cunningham et al. |
| 6,847,451 B2 | 1/2005 | Pugh |
| 6,849,052 B2 | 2/2005 | Uchigaki et al. |
| 6,890,421 B2 | 5/2005 | Ohara et al. |
| 6,896,850 B2 | 5/2005 | Subramanian et al. |
| 6,903,815 B2 | 6/2005 | Uchiyama et al. |
| 6,918,404 B2 | 7/2005 | Da Silva |
| 6,919,960 B2 | 7/2005 | Hansen et al. |
| 6,923,764 B2 | 8/2005 | Aceti et al. |
| 6,936,476 B1 | 8/2005 | Anderson et al. |
| D511,214 S | 11/2005 | Sasano et al. |
| 6,988,996 B2 | 1/2006 | Roe et al. |
| 7,004,928 B2 | 2/2006 | Aceti et al. |
| 7,011,630 B2 | 3/2006 | Desai et al. |
| 7,025,774 B2 | 4/2006 | Freeman et al. |
| D519,868 S | 5/2006 | Sasano et al. |
| 7,052,652 B2 | 5/2006 | Zanzucchi et al. |
| 7,066,586 B2 | 6/2006 | Da Silva |
| 7,066,890 B1 | 6/2006 | Lam et al. |
| 7,141,058 B2 | 11/2006 | Briggs et al. |
| 7,154,592 B2 | 12/2006 | Reynolds et al. |
| 7,156,809 B2 | 1/2007 | Quy |
| 7,163,616 B2 | 1/2007 | Vreeke et al. |
| 7,183,552 B2 | 2/2007 | Russell |
| 7,192,061 B2 | 3/2007 | Martin |
| 7,192,405 B2 | 3/2007 | DeNuzzio et al. |
| D540,343 S | 4/2007 | Cummins |
| 7,223,365 B2 | 5/2007 | Von Der Goltz |
| 7,225,008 B1 | 5/2007 | Ward et al. |
| 7,226,461 B2 | 6/2007 | Boecker et al. |
| 7,229,458 B2 | 6/2007 | Boecker et al. |
| 7,258,673 B2 | 8/2007 | Racchini et al. |
| D551,243 S | 9/2007 | Young |
| 7,270,970 B2 | 9/2007 | Anderson et al. |
| 7,297,151 B2 | 11/2007 | Boecker et al. |
| 7,299,081 B2 | 11/2007 | Mace et al. |
| 7,316,700 B2 | 1/2008 | Alden et al. |
| 7,323,141 B2 | 1/2008 | Kirchhevel et al. |
| 7,323,315 B2 | 1/2008 | Marfurt |
| 7,341,830 B2 | 3/2008 | Horn et al. |
| 7,343,188 B2 | 3/2008 | Sohrab |
| 7,344,507 B2 | 3/2008 | Briggs et al. |
| 7,377,904 B2 | 5/2008 | Conway et al. |
| 7,379,167 B2 | 5/2008 | Mawhirt et al. |

(56) References Cited

U.S. PATENT DOCUMENTS

| | | |
|---|---|---|
| 7,427,377 B2 | 9/2008 | Zanzucchi et al. |
| 7,439,033 B2 | 10/2008 | Marfurt |
| D580,068 S | 11/2008 | Shigesada et al. |
| D580,558 S | 11/2008 | Shigesada et al. |
| 7,501,053 B2 | 3/2009 | Karinka et al. |
| 7,537,571 B2 | 5/2009 | Freeman et al. |
| D599,373 S | 9/2009 | Kobayashi et al. |
| D601,257 S | 9/2009 | Berlinger et al. |
| 7,582,063 B2 | 9/2009 | Wurster et al. |
| 7,585,278 B2 | 9/2009 | Aceti et al. |
| D601,444 S | 10/2009 | Jones et al. |
| D601,578 S | 10/2009 | Poulet et al. |
| 7,655,019 B2 | 2/2010 | LeVaughn et al. |
| 7,682,318 B2 | 3/2010 | Alden et al. |
| 7,708,701 B2 | 5/2010 | Boecker et al. |
| 7,713,214 B2 | 5/2010 | Freeman et al. |
| 7,725,149 B2 | 5/2010 | Peyser et al. |
| D622,393 S | 8/2010 | Gatrall et al. |
| 7,780,631 B2 | 8/2010 | Lum et al. |
| 7,803,123 B2 | 9/2010 | Perez et al. |
| 7,819,822 B2 | 10/2010 | Calasso et al. |
| 7,841,992 B2 | 11/2010 | Freeman et al. |
| 7,850,621 B2 | 12/2010 | Briggs et al. |
| 7,879,058 B2 | 2/2011 | Ikeda |
| 7,883,473 B2 | 2/2011 | LeVaughn et al. |
| 7,887,494 B2 | 2/2011 | Emery et al. |
| 7,892,183 B2 | 2/2011 | Boecker et al. |
| 7,955,492 B2 | 6/2011 | Fujiwara et al. |
| 7,959,583 B2 | 6/2011 | DeNuzzio et al. |
| 7,964,372 B2 | 6/2011 | Marfurt |
| D642,191 S | 7/2011 | Barnett et al. |
| 7,972,861 B2 | 7/2011 | Deng et al. |
| 7,988,644 B2 | 8/2011 | Freeman et al. |
| 8,012,103 B2 | 9/2011 | Escutia et al. |
| 8,012,104 B2 | 9/2011 | Escutia et al. |
| 8,105,849 B2 | 1/2012 | McDevitt et al. |
| D654,926 S | 2/2012 | Lipman et al. |
| 8,173,439 B2 | 5/2012 | Petrich et al. |
| 8,184,273 B2 | 5/2012 | Dosmann et al. |
| 8,202,231 B2 | 6/2012 | Freeman et al. |
| 8,231,832 B2 | 7/2012 | Zanzucchi et al. |
| 8,251,920 B2 | 8/2012 | Vreeke et al. |
| 8,262,614 B2 | 9/2012 | Freeman et al. |
| 8,267,870 B2 | 9/2012 | Freeman et al. |
| 8,280,476 B2 | 10/2012 | Jina |
| 8,298,255 B2 | 10/2012 | Conway et al. |
| 8,303,518 B2 | 11/2012 | Aceti et al. |
| 8,360,993 B2 | 1/2013 | Escutia et al. |
| 8,360,994 B2 | 1/2013 | Escutia et al. |
| 8,372,015 B2 | 2/2013 | Escutia et al. |
| 8,372,016 B2 | 2/2013 | Freeman et al. |
| 8,376,959 B2 | 2/2013 | Deck |
| 8,382,680 B2 | 2/2013 | Kistner et al. |
| 8,382,681 B2 | 2/2013 | Escutia et al. |
| 8,391,940 B2 | 3/2013 | Matzinger et al. |
| 8,419,657 B2 | 4/2013 | Roe |
| D691,174 S | 10/2013 | Lipman et al. |
| 8,574,168 B2 | 11/2013 | Freeman et al. |
| 8,574,895 B2 | 11/2013 | Freeman et al. |
| 8,696,880 B2 | 4/2014 | Beer et al. |
| 8,702,624 B2 | 4/2014 | Alden |
| 8,795,201 B2 | 8/2014 | Escutia et al. |
| 8,801,631 B2 | 8/2014 | Escutia et al. |
| 8,919,605 B2 | 12/2014 | Lipman et al. |
| 8,920,455 B2 | 12/2014 | Roe |
| 8,969,097 B2 | 3/2015 | Emery et al. |
| 9,017,356 B2 | 4/2015 | Schraga et al. |
| 9,034,639 B2 | 5/2015 | Freeman et al. |
| 9,060,723 B2 | 6/2015 | Escutia et al. |
| 9,060,727 B2 | 6/2015 | Saikley et al. |
| 9,063,102 B2 | 6/2015 | Hoenes et al. |
| 9,089,678 B2 | 7/2015 | Freeman et al. |
| 9,095,292 B2 | 8/2015 | Zanzucchi et al. |
| 9,095,847 B2 | 8/2015 | Porsch et al. |
| 9,097,679 B2 | 8/2015 | List et al. |
| 9,101,302 B2 | 8/2015 | Mace et al. |
| 9,131,886 B2 | 9/2015 | Harttig et al. |
| 9,138,179 B2 | 9/2015 | Hoenes et al. |
| 9,149,215 B2 | 10/2015 | Werner et al. |
| 9,173,608 B2 | 11/2015 | Kuhr et al. |
| 9,179,872 B2 | 11/2015 | Roe et al. |
| 9,186,097 B2 | 11/2015 | Frey et al. |
| 9,186,104 B2 | 11/2015 | Kraemer et al. |
| 9,186,468 B2 | 11/2015 | Freeman et al. |
| 9,226,704 B2 | 1/2016 | Deck |
| 9,301,171 B2 | 4/2016 | List et al. |
| 9,314,194 B2 | 4/2016 | Deshmukh et al. |
| 9,326,718 B2 | 5/2016 | Petrich et al. |
| 9,332,931 B2 | 5/2016 | Chan |
| 9,332,932 B2 | 5/2016 | Okuyama et al. |
| 9,339,612 B2 | 5/2016 | Freeman et al. |
| 9,351,680 B2 | 5/2016 | Boecker et al. |
| 9,364,172 B2 | 6/2016 | Konya et al. |
| 9,366,636 B2 | 6/2016 | Emery et al. |
| 9,375,169 B2 | 6/2016 | Choi et al. |
| 9,375,177 B2 | 6/2016 | Planman et al. |
| 9,380,963 B2 | 7/2016 | Gofman et al. |
| 9,380,974 B2 | 7/2016 | Litherland et al. |
| 9,386,944 B2 | 7/2016 | Freeman et al. |
| 9,392,968 B2 | 7/2016 | Schraga |
| 9,439,591 B2 | 9/2016 | Frey et al. |
| 9,463,463 B2 | 10/2016 | He et al. |
| 9,480,419 B2 | 11/2016 | Weiss et al. |
| 9,480,420 B2 | 11/2016 | Konya et al. |
| 9,486,164 B2 | 11/2016 | Roe |
| 9,488,585 B2 | 11/2016 | Emeric et al. |
| 9,517,027 B2 | 12/2016 | Kan et al. |
| 9,560,993 B2 | 2/2017 | Freeman |
| 9,561,000 B2 | 2/2017 | Lum |
| 9,573,761 B2 | 2/2017 | List |
| 9,599,552 B2 | 3/2017 | Baldus et al. |
| 9,603,562 B2 | 3/2017 | Aceti et al. |
| 9,636,051 B2 | 5/2017 | Emery et al. |
| 9,668,687 B2 | 6/2017 | Volkmuth et al. |
| 9,671,387 B2 | 6/2017 | Thoes et al. |
| 9,717,452 B2 | 8/2017 | Roe et al. |
| 9,724,021 B2 | 8/2017 | Freeman et al. |
| 9,730,625 B2 | 8/2017 | Krasnow et al. |
| 9,782,114 B2 | 10/2017 | Reynolds et al. |
| 9,795,334 B2 | 10/2017 | Freeman et al. |
| 9,820,684 B2 | 11/2017 | Freeman et al. |
| 9,833,183 B2 | 12/2017 | Escutia et al. |
| 9,839,384 B2 | 12/2017 | Escutia et al. |
| 9,877,676 B2 | 1/2018 | Konya et al. |
| 9,880,254 B2 | 1/2018 | Richter et al. |
| 9,883,828 B2 | 2/2018 | Haar et al. |
| 9,897,610 B2 | 2/2018 | Lipman et al. |
| 9,927,386 B2 | 3/2018 | Wang et al. |
| 9,931,478 B2 | 4/2018 | Hirshberg et al. |
| 9,939,403 B2 | 4/2018 | Richter et al. |
| 9,939,404 B2 | 4/2018 | Richter et al. |
| 9,943,256 B2 | 4/2018 | Varsavsky et al. |
| 9,943,259 B2 | 4/2018 | Kuhr et al. |
| 9,949,679 B2 | 4/2018 | Renlund |
| 9,965,587 B2 | 5/2018 | Aykroyd et al. |
| 9,968,284 B2 | 5/2018 | Vidalis et al. |
| 9,974,471 B1 | 5/2018 | Kam et al. |
| 9,983,140 B2 | 5/2018 | Dickopf |
| 9,987,427 B1 | 6/2018 | Polsky et al. |
| 10,034,628 B2 | 7/2018 | Freeman et al. |
| 10,080,517 B2 | 9/2018 | Chen et al. |
| 10,194,838 B2 | 2/2019 | Weiss et al. |
| 10,226,208 B2 | 3/2019 | Emery et al. |
| 10,278,621 B2 | 5/2019 | List |
| 10,309,905 B2 | 6/2019 | Dickopf |
| 10,327,689 B2 | 6/2019 | Krasnow et al. |
| 10,330,667 B2 | 6/2019 | Lipman et al. |
| 10,383,556 B2 | 8/2019 | Lipman et al. |
| 10,429,337 B2 | 10/2019 | Malecha et al. |
| 10,433,780 B2 | 10/2019 | Escutia et al. |
| 10,441,205 B2 | 10/2019 | Litherland et al. |
| 10,729,386 B2 | 8/2020 | Lipman et al. |
| 10,772,550 B2 | 9/2020 | Aceti et al. |
| 10,842,427 B2 | 11/2020 | Escutia et al. |

(56) References Cited

U.S. PATENT DOCUMENTS

| | | |
|---|---|---|
| 11,002,743 B2 | 5/2021 | Lipman et al. |
| 11,051,734 B2 | 7/2021 | Escutia et al. |
| 2001/0001034 A1 | 5/2001 | Douglas |
| 2001/0027328 A1 | 10/2001 | Lum et al. |
| 2001/0053891 A1 | 12/2001 | Ackley |
| 2002/0002326 A1 | 1/2002 | Causey, III et al. |
| 2002/0002344 A1 | 1/2002 | Douglas et al. |
| 2002/0004640 A1 | 1/2002 | Conn et al. |
| 2002/0006355 A1 | 1/2002 | Whitson |
| 2002/0016568 A1 | 2/2002 | Lebel et al. |
| 2002/0020688 A1 | 2/2002 | Sherman et al. |
| 2002/0022934 A1 | 2/2002 | Vogel et al. |
| 2002/0023852 A1 | 2/2002 | Mcivor et al. |
| 2002/0042594 A1 | 4/2002 | Lum et al. |
| 2002/0045243 A1 | 4/2002 | Laska et al. |
| 2002/0052618 A1 | 5/2002 | Haar et al. |
| 2002/0067481 A1 | 6/2002 | Wolf et al. |
| 2002/0087056 A1 | 7/2002 | Aceti et al. |
| 2002/0136667 A1 | 9/2002 | Subramanian et al. |
| 2002/0137998 A1 | 9/2002 | Smart et al. |
| 2002/0160520 A1 | 10/2002 | Orloff et al. |
| 2002/0168290 A1 | 11/2002 | Yuzhakov et al. |
| 2002/0169394 A1 | 11/2002 | Eppstein et al. |
| 2002/0169411 A1 | 11/2002 | Sherman et al. |
| 2002/0177761 A1 | 11/2002 | Orloff et al. |
| 2002/0177764 A1 | 11/2002 | Sohrab |
| 2002/0183102 A1 | 12/2002 | Withers et al. |
| 2002/0188223 A1 | 12/2002 | Perez et al. |
| 2002/0198444 A1 | 12/2002 | Uchigaki et al. |
| 2003/0012693 A1 | 1/2003 | Otillar et al. |
| 2003/0028087 A1 | 2/2003 | Yuzhakov et al. |
| 2003/0028125 A1 | 2/2003 | Yuzhakov et al. |
| 2003/0039587 A1 | 2/2003 | Niermann |
| 2003/0060730 A1 | 3/2003 | Perez |
| 2003/0083685 A1 | 5/2003 | Freeman et al. |
| 2003/0083686 A1 | 5/2003 | Freeman et al. |
| 2003/0105961 A1 | 6/2003 | Zatloukal et al. |
| 2003/0116596 A1 | 6/2003 | Terasawa |
| 2003/0135166 A1 | 7/2003 | Gonnelli |
| 2003/0135333 A1 | 7/2003 | Aceti |
| 2003/0143746 A1 | 7/2003 | Sage |
| 2003/0153844 A1 | 8/2003 | Smith et al. |
| 2003/0153900 A1 | 8/2003 | Aceti et al. |
| 2003/0175987 A1 | 9/2003 | Verdonk et al. |
| 2003/0187395 A1 | 10/2003 | Gabel et al. |
| 2003/0206302 A1 | 11/2003 | Pugh |
| 2003/0207441 A1 | 11/2003 | Eyster et al. |
| 2003/0208113 A1 | 11/2003 | Mault et al. |
| 2003/0208140 A1* | 11/2003 | Pugh ............... A61B 5/150022 600/584 |
| 2003/0211617 A1 | 11/2003 | Jones |
| 2003/0211619 A1 | 11/2003 | Olson et al. |
| 2003/0212344 A1 | 11/2003 | Yuzhakov et al. |
| 2003/0212345 A1 | 11/2003 | McAllister et al. |
| 2003/0212347 A1 | 11/2003 | Sohrab |
| 2003/0216628 A1 | 11/2003 | Bortz et al. |
| 2004/0010207 A1 | 1/2004 | Flaherty et al. |
| 2004/0030353 A1 | 2/2004 | Schmelzeisen-redeker et al. |
| 2004/0039303 A1 | 2/2004 | Wurster et al. |
| 2004/0049219 A1 | 3/2004 | Briggs et al. |
| 2004/0059256 A1 | 3/2004 | Perez |
| 2004/0072357 A1 | 4/2004 | Stiene et al. |
| 2004/0073140 A1 | 4/2004 | Douglas |
| 2004/0092842 A1 | 5/2004 | Boecker et al. |
| 2004/0092995 A1 | 5/2004 | Boecker et al. |
| 2004/0094432 A1 | 5/2004 | Neel et al. |
| 2004/0096959 A1 | 5/2004 | Stiene et al. |
| 2004/0097796 A1 | 5/2004 | Berman et al. |
| 2004/0098009 A1 | 5/2004 | Boecker et al. |
| 2004/0102803 A1 | 5/2004 | Boecker et al. |
| 2004/0120848 A1 | 6/2004 | Teodorczyk |
| 2004/0122339 A1 | 6/2004 | Roe et al. |
| 2004/0132167 A1 | 7/2004 | Rule et al. |
| 2004/0138588 A1 | 7/2004 | Saikley et al. |
| 2004/0155084 A1 | 8/2004 | Brown |
| 2004/0157339 A1 | 8/2004 | Burke et al. |
| 2004/0178218 A1 | 9/2004 | Schomakers et al. |
| 2004/0186394 A1 | 9/2004 | Roe et al. |
| 2004/0191119 A1 | 9/2004 | Zanzucchi et al. |
| 2004/0202576 A1 | 10/2004 | Aceti et al. |
| 2004/0230216 A1 | 11/2004 | LeVaughn et al. |
| 2004/0230316 A1 | 11/2004 | LeVaughn et al. |
| 2004/0236251 A1 | 11/2004 | Roe et al. |
| 2004/0238675 A1 | 12/2004 | Banaszkiewicz et al. |
| 2004/0242982 A1 | 12/2004 | Sakata et al. |
| 2004/0249253 A1 | 12/2004 | Racchini et al. |
| 2004/0259180 A1 | 12/2004 | Burke et al. |
| 2005/0004494 A1 | 1/2005 | Perez et al. |
| 2005/0010134 A1 | 1/2005 | Douglas et al. |
| 2005/0015020 A1 | 1/2005 | LeVaughn et al. |
| 2005/0027182 A1 | 2/2005 | Siddiqui et al. |
| 2005/0033340 A1 | 2/2005 | Lipoma et al. |
| 2005/0038680 A1 | 2/2005 | McMahon |
| 2005/0070819 A1 | 3/2005 | Poux et al. |
| 2005/0096686 A1 | 5/2005 | Allen |
| 2005/0106713 A1 | 5/2005 | Phan et al. |
| 2005/0109386 A1 | 5/2005 | Marshall |
| 2005/0153428 A1 | 7/2005 | Matsumoto |
| 2005/0154410 A1 | 7/2005 | Conway et al. |
| 2005/0159678 A1 | 7/2005 | Taniike et al. |
| 2005/0176133 A1 | 8/2005 | Miyashita et al. |
| 2005/0187532 A1 | 8/2005 | Thurau et al. |
| 2005/0192492 A1 | 9/2005 | Cho et al. |
| 2005/0202567 A1 | 9/2005 | Zanzucchi et al. |
| 2005/0202733 A1 | 9/2005 | Yoshimura et al. |
| 2005/0209518 A1 | 9/2005 | Sage et al. |
| 2005/0215872 A1 | 9/2005 | Berner et al. |
| 2005/0215923 A1 | 9/2005 | Wiegel |
| 2005/0234494 A1 | 10/2005 | Conway et al. |
| 2005/0245844 A1 | 11/2005 | Mace et al. |
| 2005/0255001 A1 | 11/2005 | Padmaabhan et al. |
| 2005/0277972 A1 | 12/2005 | Wong et al. |
| 2006/0008389 A1 | 1/2006 | Sacherer et al. |
| 2006/0036134 A1 | 2/2006 | Tarassenko et al. |
| 2006/0052724 A1 | 3/2006 | Roe |
| 2006/0064035 A1 | 3/2006 | Wang et al. |
| 2006/0079809 A1 | 4/2006 | Goldberger et al. |
| 2006/0094985 A1 | 5/2006 | Aceti et al. |
| 2006/0117616 A1 | 6/2006 | Jones et al. |
| 2006/0122536 A1 | 6/2006 | Haar et al. |
| 2006/0135873 A1 | 6/2006 | Karo et al. |
| 2006/0155317 A1 | 7/2006 | List |
| 2006/0161078 A1 | 7/2006 | Schraga |
| 2006/0178600 A1 | 8/2006 | Kennedy et al. |
| 2006/0189908 A1 | 8/2006 | Kennedy |
| 2006/0200044 A1 | 9/2006 | Freeman et al. |
| 2006/0204399 A1 | 9/2006 | Freeman et al. |
| 2006/0224172 A1 | 10/2006 | LeVaughn et al. |
| 2006/0229533 A1 | 10/2006 | Hoenes et al. |
| 2006/0241517 A1 | 10/2006 | Fowler et al. |
| 2006/0257993 A1 | 11/2006 | Mcdevitt et al. |
| 2006/0259102 A1 | 11/2006 | Slatkine |
| 2006/0264996 A1 | 11/2006 | LeVaughn et al. |
| 2006/0281187 A1 | 12/2006 | Emery et al. |
| 2007/0016104 A1 | 1/2007 | Jansen et al. |
| 2007/0017824 A1 | 1/2007 | Rippeth et al. |
| 2007/0033074 A1 | 2/2007 | Nitzan et al. |
| 2007/0060842 A1 | 3/2007 | Alvarez-Icaza et al. |
| 2007/0078313 A1 | 4/2007 | Emery et al. |
| 2007/0078358 A1 | 4/2007 | Escutia et al. |
| 2007/0083130 A1 | 4/2007 | Thomson et al. |
| 2007/0083131 A1 | 4/2007 | Escutia et al. |
| 2007/0093786 A1 | 4/2007 | Goldsmith et al. |
| 2007/0100255 A1 | 5/2007 | Boecker et al. |
| 2007/0112281 A1 | 5/2007 | Olson |
| 2007/0179404 A1 | 8/2007 | Escutia et al. |
| 2007/0253531 A1 | 11/2007 | Okuzawa et al. |
| 2007/0255181 A1 | 11/2007 | Alvarez-icaza et al. |
| 2007/0255302 A1 | 11/2007 | Koeppel et al. |
| 2008/0012701 A1 | 1/2008 | Kass et al. |
| 2008/0046831 A1 | 2/2008 | Imai et al. |
| 2008/0064986 A1 | 3/2008 | Kraemer et al. |
| 2008/0077048 A1 | 3/2008 | Escutia et al. |
| 2008/0119702 A1 | 5/2008 | Reggiardo |

(56) References Cited

U.S. PATENT DOCUMENTS

| | | |
|---|---|---|
| 2008/0139910 A1 | 6/2008 | Mastrototaro et al. |
| 2008/0194934 A1 | 8/2008 | Ray et al. |
| 2008/0200838 A1* | 8/2008 | Goldberger ...... A61B 5/150633 600/583 |
| 2008/0255598 A1 | 10/2008 | LeVaughn et al. |
| 2008/0268485 A1 | 10/2008 | Guarino et al. |
| 2008/0269625 A1 | 10/2008 | Halperin et al. |
| 2008/0274447 A1 | 11/2008 | Mecklenburg |
| 2009/0054810 A1 | 2/2009 | Zanzucchi et al. |
| 2009/0149717 A1 | 6/2009 | Brauer et al. |
| 2009/0149729 A1 | 6/2009 | Young et al. |
| 2009/0156923 A1 | 6/2009 | Power et al. |
| 2009/0292489 A1 | 11/2009 | Burke et al. |
| 2009/0301899 A1 | 12/2009 | Hodges et al. |
| 2010/0010374 A1 | 1/2010 | Escutia et al. |
| 2010/0021947 A1 | 1/2010 | Emery et al. |
| 2010/0021948 A1 | 1/2010 | Lipman et al. |
| 2010/0095229 A1 | 4/2010 | Dixon et al. |
| 2010/0152660 A1 | 6/2010 | Mack et al. |
| 2010/0174211 A1 | 7/2010 | Frey et al. |
| 2010/0185120 A1 | 7/2010 | Sacherer et al. |
| 2010/0217155 A1 | 8/2010 | Poux et al. |
| 2010/0249652 A1 | 9/2010 | Rush et al. |
| 2010/0331650 A1 | 12/2010 | Batman et al. |
| 2011/0098599 A1 | 4/2011 | Emery et al. |
| 2011/0105872 A1 | 5/2011 | Chickering et al. |
| 2011/0294152 A1 | 12/2011 | Lipman et al. |
| 2012/0166090 A1 | 6/2012 | Lipman et al. |
| 2012/0271197 A1 | 10/2012 | Castle et al. |
| 2012/0296179 A1 | 11/2012 | Zanzucchi et al. |
| 2013/0110516 A1 | 5/2013 | Abulhaj et al. |
| 2013/0158430 A1 | 6/2013 | Aceti et al. |
| 2013/0158432 A1 | 6/2013 | Escutia et al. |
| 2013/0172698 A1 | 7/2013 | Reynolds et al. |
| 2013/0274568 A1 | 10/2013 | Escutia et al. |
| 2013/0274579 A1 | 10/2013 | Richter et al. |
| 2014/0012116 A1 | 1/2014 | Okuyama |
| 2014/0316301 A1 | 10/2014 | Escutia et al. |
| 2014/0336480 A1 | 11/2014 | Escutia et al. |
| 2014/0376762 A1 | 12/2014 | Lipman et al. |
| 2015/0037898 A1 | 2/2015 | Baldus et al. |
| 2015/0153351 A1 | 6/2015 | Lipman et al. |
| 2015/0182157 A1 | 7/2015 | Boriah et al. |
| 2015/0238131 A1 | 8/2015 | Richter et al. |
| 2015/0268228 A1 | 9/2015 | Schulat et al. |
| 2015/0335272 A1 | 11/2015 | Natale et al. |
| 2016/0011178 A1 | 1/2016 | Hoenes et al. |
| 2016/0038066 A1 | 2/2016 | Escutia et al. |
| 2016/0256106 A1 | 9/2016 | Krasnow et al. |
| 2016/0367178 A1 | 12/2016 | Litherland et al. |
| 2016/0374603 A1 | 12/2016 | Shaanan et al. |
| 2017/0095188 A1 | 4/2017 | Emery et al. |
| 2017/0319121 A1 | 11/2017 | Aceti et al. |
| 2018/0008178 A1 | 1/2018 | Escutia et al. |
| 2018/0214059 A1 | 8/2018 | Escutia et al. |
| 2018/0296143 A1 | 10/2018 | Anderson et al. |
| 2018/0310865 A1 | 11/2018 | Escutia et al. |
| 2018/0338713 A1 | 11/2018 | Polsky et al. |
| 2019/0000365 A1 | 1/2019 | Beyerlein et al. |
| 2019/0025318 A1 | 1/2019 | Lipman et al. |
| 2019/0104976 A1 | 4/2019 | Reynolds et al. |
| 2019/0175086 A1 | 6/2019 | Yang |
| 2019/0209064 A1 | 7/2019 | Emery et al. |
| 2019/0209820 A1 | 7/2019 | Chickering, III et al. |
| 2019/0269358 A1 | 9/2019 | Messerschmidt |
| 2019/0274607 A1 | 9/2019 | Krasnow et al. |
| 2019/0391129 A1 | 12/2019 | Lipman et al. |
| 2020/0214605 A1 | 7/2020 | Lipman et al. |
| 2020/0237280 A1 | 7/2020 | Escutia et al. |
| 2021/0177361 A1 | 6/2021 | Lipman et al. |
| 2021/0330225 A1 | 10/2021 | Escutia et al. |

FOREIGN PATENT DOCUMENTS

| | | |
|---|---|---|
| DE | 103 02-501 A1 | 8/2004 |
| EP | 0103426 A2 | 3/1984 |
| EP | 0 256 806 A2 | 2/1988 |
| EP | 0 160 708 B1 | 10/1989 |
| EP | 0 356 418 A2 | 2/1990 |
| EP | 0 396-016 A2 | 11/1990 |
| EP | 0 396-016 A3 | 11/1990 |
| EP | 0 409 032 A2 | 1/1991 |
| EP | 0 255-338 A2 | 2/1998 |
| EP | 0 877 250 A2 | 11/1998 |
| EP | 1 037 048 A2 | 9/2000 |
| EP | 1 060 768 A2 | 12/2000 |
| EP | 1 118 856 A1 | 7/2001 |
| EP | 1 266-607 A2 | 12/2002 |
| EP | 1 266-607 A3 | 12/2002 |
| EP | 1 369 688 A2 | 10/2003 |
| EP | 1 369 688 A3 | 10/2003 |
| EP | 1 360-934 A1 | 11/2003 |
| EP | 1 360-934 B1 | 11/2003 |
| EP | 1 486-766 A1 | 12/2004 |
| EP | 1 486-766 B1 | 12/2004 |
| EP | 1 529-489 A1 | 5/2005 |
| EP | 1 529-489 B1 | 5/2005 |
| EP | 1 769-735 A1 | 4/2007 |
| EP | 1 987 766 A2 | 11/2008 |
| JP | 61-290342 A | 12/1986 |
| JP | 63-305841 A | 12/1988 |
| JP | 1-318963 A | 12/1989 |
| JP | 3-63570 A | 3/1991 |
| JP | 03093189 A | 4/1991 |
| JP | 7-67861 A | 3/1995 |
| JP | 7-213925 A | 8/1995 |
| JP | 9-168530 A | 6/1997 |
| JP | 9-313465 A | 9/1997 |
| JP | 9-266889 A | 10/1997 |
| JP | 9-294737 A | 11/1997 |
| JP | 10-024028 A | 1/1998 |
| JP | 10-318970 A | 12/1998 |
| JP | 11-056822 A | 3/1999 |
| JP | 11281779 A | 10/1999 |
| JP | 2000-116629 A | 4/2000 |
| JP | 2000-126161 A | 5/2000 |
| JP | 2000-168754 A | 6/2000 |
| JP | 2000-254111 A | 9/2000 |
| JP | 2001-159618 A | 6/2001 |
| JP | 2001-515203 A | 9/2001 |
| JP | 2001-281242 A | 10/2001 |
| JP | 2001-305096 A | 10/2001 |
| JP | 2001-330581 A | 11/2001 |
| JP | 2002-502045 A | 1/2002 |
| JP | 2002-085384 A | 3/2002 |
| JP | 2002-514453 A | 5/2002 |
| JP | 2002-168862 A | 6/2002 |
| JP | 2003-507719 A | 2/2003 |
| JP | 2003/108679 A | 4/2003 |
| JP | 2003-180417 A2 | 7/2003 |
| JP | 2004-000598 A | 1/2004 |
| JP | 2004-500948 A | 1/2004 |
| JP | 2004-117339 A | 4/2004 |
| JP | 2004-209266 A | 7/2004 |
| JP | 2004-519302 A | 7/2004 |
| JP | 2004-522500 A | 7/2004 |
| JP | 2004-528936 A | 9/2004 |
| JP | 2005-503538 A | 2/2005 |
| JP | 2005-087613 A | 4/2005 |
| JP | 2006-512969 A | 4/2005 |
| JP | 2005-525149 A | 8/2005 |
| JP | 2005-237938 A | 9/2005 |
| JP | 2005-525846 A | 9/2005 |
| JP | 2005-527254 A | 9/2005 |
| JP | 2006-512974 A | 4/2006 |
| JP | 2006-516723 A | 7/2006 |
| JP | 2006-521555 A | 9/2006 |
| JP | 2006-284481 A | 10/2006 |
| JP | 2006-527013 A | 11/2006 |
| JP | 2007-054407 A | 3/2007 |
| JP | 2007-067698 A | 3/2007 |

(56) References Cited

FOREIGN PATENT DOCUMENTS

| | | |
|---|---|---|
| JP | 2007-521031 A | 8/2007 |
| JP | 2007-527287 A | 9/2007 |
| JP | 2007-311196 A | 11/2007 |
| JP | 2008-043741 A | 2/2008 |
| JP | 2008-125813 A | 6/2008 |
| JP | 2008-212324 A | 9/2008 |
| JP | 2009-509645 A | 3/2009 |
| JP | 2009-509667 A | 3/2009 |
| JP | 2012-213477 A | 11/2012 |
| JP | 2013-505747 A | 2/2013 |
| KR | 100458978 B1 | 5/2005 |
| WO | WO-88/07666 A1 | 10/1988 |
| WO | WO-91/14212 A1 | 9/1991 |
| WO | WO-94/13203 A1 | 6/1994 |
| WO | WO-95/10223 A2 | 4/1995 |
| WO | WO-95/10223 A3 | 4/1995 |
| WO | WO-96/04857 A1 | 2/1996 |
| WO | WO-96/07907 A1 | 3/1996 |
| WO | WO-96/14026 A1 | 5/1996 |
| WO | WO-96/25088 A1 | 8/1996 |
| WO | WO-97/15227 A1 | 5/1997 |
| WO | WO-97/29847 A1 | 8/1997 |
| WO | WO-97/30344 A1 | 8/1997 |
| WO | WO-97/41421 A1 | 11/1997 |
| WO | WO-98/31275 A1 | 7/1998 |
| WO | WO-98/35225 A1 | 8/1998 |
| WO | WO-99/12008 A1 | 3/1999 |
| WO | WO-99/44508 A1 | 9/1999 |
| WO | WO-99/58051 A1 | 11/1999 |
| WO | WO-00/09184 A1 | 2/2000 |
| WO | WO-00/13573 A1 | 3/2000 |
| WO | WO-00/14269 A1 | 3/2000 |
| WO | WO-00/14535 A1 | 3/2000 |
| WO | WO-00/18449 A2 | 4/2000 |
| WO | WO-00/18449 A3 | 4/2000 |
| WO | WO-00/19185 | 4/2000 |
| WO | WO-00/36400 A1 | 6/2000 |
| WO | WO-00/42422 A1 | 7/2000 |
| WO | WO-00/74763 A2 | 12/2000 |
| WO | WO-00/74763 A3 | 12/2000 |
| WO | WO-00/78208 A1 | 12/2000 |
| WO | WO-01/13795 A1 | 3/2001 |
| WO | WO-01/16575 A1 | 3/2001 |
| WO | WO-01/52727 A1 | 7/2001 |
| WO | WO-01/64105 A1 | 9/2001 |
| WO | WO-01/64105 C2 | 9/2001 |
| WO | WO-01/72220 A1 | 10/2001 |
| WO | WO-01/80728 A1 | 11/2001 |
| WO | WO-01/85233 A2 | 11/2001 |
| WO | WO-01/85233 A3 | 11/2001 |
| WO | WO-01/91634 A2 | 12/2001 |
| WO | WO-01/91634 A3 | 12/2001 |
| WO | WO-02/00101 A2 | 1/2002 |
| WO | WO-02/00101 A3 | 1/2002 |
| WO | WO-02/49507 A1 | 6/2002 |
| WO | WO-02/49509 A2 | 6/2002 |
| WO | WO-02/49509 A3 | 6/2002 |
| WO | WO-02/078533 A2 | 10/2002 |
| WO | WO-02/078533 A3 | 10/2002 |
| WO | WO-02/082052 A2 | 10/2002 |
| WO | WO-02/082052 A3 | 10/2002 |
| WO | WO-02/093144 A1 | 11/2002 |
| WO | WO-02/100251 A2 | 12/2002 |
| WO | WO-02/100251 A3 | 12/2002 |
| WO | WO-02/101359 A2 | 12/2002 |
| WO | WO-02/101359 A3 | 12/2002 |
| WO | WO-03/007819 A1 | 1/2003 |
| WO | WO-2003/030984 A1 | 4/2003 |
| WO | WO-2003/066128 A2 | 8/2003 |
| WO | WO-2003/066128 A3 | 8/2003 |
| WO | WO-2003/070099 A1 | 8/2003 |
| WO | WO-2003/071940 A1 | 9/2003 |
| WO | WO-2003/071940 C1 | 9/2003 |
| WO | WO-03/088834 A1 | 10/2003 |
| WO | WO-2004/062499 A1 | 7/2004 |
| WO | WO-2004/062500 A1 | 7/2004 |
| WO | WO-2004/062500 C1 | 7/2004 |
| WO | WO-2004/064636 A1 | 8/2004 |
| WO | WO-2004/085995 A2 | 10/2004 |
| WO | WO-2004/085995 A3 | 10/2004 |
| WO | WO-2004/091693 A2 | 10/2004 |
| WO | WO-2004/091693 A3 | 10/2004 |
| WO | WO-2005/006939 A2 | 1/2005 |
| WO | WO-2005/006939 A3 | 1/2005 |
| WO | WO-2005/009238 A1 | 2/2005 |
| WO | WO-2005/018709 A2 | 3/2005 |
| WO | WO-2005/018709 A3 | 3/2005 |
| WO | WO-2005/054840 A1 | 6/2005 |
| WO | WO-2005/084546 A2 | 9/2005 |
| WO | WO-2005/084546 A3 | 9/2005 |
| WO | WO-2005/085995 A1 | 9/2005 |
| WO | WO-2006/031920 A2 | 3/2006 |
| WO | WO-2006/138226 A2 | 12/2006 |
| WO | WO-2006/138226 A3 | 12/2006 |
| WO | WO-2007/041062 A2 | 4/2007 |
| WO | WO-2007/041062 A3 | 4/2007 |
| WO | WO-2007/041063 A2 | 4/2007 |
| WO | WO-2007/041063 A3 | 4/2007 |
| WO | WO-2007/041244 A2 | 4/2007 |
| WO | WO-2007/041244 A3 | 4/2007 |
| WO | WO-2007/041287 A2 | 4/2007 |
| WO | WO-2007/041287 A3 | 4/2007 |
| WO | WO-2007/041355 A2 | 4/2007 |
| WO | WO-2007/041355 A3 | 4/2007 |
| WO | WO-2007/054317 A1 | 5/2007 |
| WO | WO-2007/108519 A1 | 9/2007 |
| WO | WO-2007/112034 A2 | 10/2007 |
| WO | WO-2007/112034 A3 | 10/2007 |
| WO | WO 2007131036 * | 11/2007 |
| WO | WO-2008/027319 A2 | 3/2008 |
| WO | WO-2008/027319 A3 | 3/2008 |
| WO | WO-2008/062648 A1 | 5/2008 |
| WO | WO-2009/145920 A1 | 12/2009 |
| WO | WO-2009/148624 A1 | 12/2009 |
| WO | WO-2009/148626 A1 | 12/2009 |
| WO | WO-2011/065981 A1 | 6/2011 |
| WO | WO-2011/162823 A1 | 12/2011 |
| WO | WO-2012/127870 A1 | 9/2012 |
| WO | WO-2013/020103 A1 | 2/2013 |
| WO | WO-2014/205412 A1 | 12/2014 |
| WO | WO-2005/018710 A2 | 3/2015 |
| WO | WO-2005/018710 A3 | 3/2015 |
| WO | WO-2018/191700 A1 | 10/2018 |

OTHER PUBLICATIONS

ADA (Jan. 1994). "Self-Monitoring of Blood Glucose," Consensus Statement *Diabetes Care* 17(1):81-86.

Anonymous. (Sep. 30, 1993). "The Effect of Intensive Treatment of Diabetes on the Development and Progression of Long-Term Complications in Insulin-Dependent Diabetes Mellitus." *The New England Journal of Medicine* 329(14):977-986.

Anonymous. (Jun. 23, 1998). Taking the "Ouch" Out of Needles: Arrays of "Microneedles" Offer New Techniques for Drug Delivery, *Science Daily,* located at <http:www.sciencedaily.com/releases/1998/06/980623045850.htm>, last visited Jan. 14, 2014, 3 pages.

Beregszàszi, M. et al. (Jul. 1997). "Nocturnal Hypoglycemia in Children and Adolescents with Insulin-Dependent Diabetes Mellitus: Prevalence and Risk Factors," *J. Pediatrics* 131(1 Pt. 1):27-33.

Brazzle, J. et al. Active Microneedles with Integrated Functionality, Solid-State Sensor and Actuator Workshop, Hilton Head Island, South Carolina, Jun. 4-8, 2000, Technical Digest, 199-202.

Chase, H.P. et al. (Feb. 2001). "Continuous Subcutaneous Glucose Monitoring in Children with Type 1 Diabetes," *Pediatrics* 107(2):222-226.

Clarke, W.L. et al. (Sep.-Oct. 1987). "Evaluating Clinical Accuracy of Systems for Self-Monitoring of Blood Glucose," *Diabetes Care* 10(5):622-628.

Clarke, W.L. et al. (1981). "Evaluation of a New Reflectance Photometer for Use in Home Blood Glucose Monitoring," *Diabetes Care* 4(5):547-550.

(56) References Cited

OTHER PUBLICATIONS

Collison, M.E. et al. (Sep. 1999). "Analytical Characterization of Electrochemical Biosensor Test Strips for Measurement of Glucose in Low-Volume Interstitial Fluid Samples," *Clinical Chemistry* 45(9):1665-1673.

Coster, S. et al. (2000). "Monitoring Blood Glucose Control in Diabetes Mellitus: A Systematic Review." *Health Technology Assessment* 4(12):1-93.

Cox, D.J. et al. (Jun. 1997). "Understanding Error Grid Analysis," *Diabetes Care* 20(6):911-912.

D'Arrigo, T.D. (Mar. 2000). "GlucoWatch Monitor Poised for Approval," *Diabetes Forecast,* 53(3):43-44.

Extended European Search Report dated Jun. 16, 2014, for EP Application No. 09 758 787.7, filed on Jun. 8, 2009, 6 pages.

Extended European Search Report dated Jul. 18, 2013, for EP Application No. 06 772 943.4, filed on Jun. 13, 2006, 7 pages.

Extended European Search Report dated Aug. 27, 2012, for European Patent Application No. 09 758 789.3, filed on Jun. 8, 2009, 13 pages.

Extended European Search Report dated Oct. 27, 2016, for EP Application No. 11 798 518.4, filed on Jun. 24, 2011, 7 pages.

Final Office Action dated May 8, 2012, for U.S. Appl. No. 12/457,331, filed Jun. 8, 2009, 7 pages.

Final Office Action dated Dec. 26, 2014, for U.S. Appl. No. 12/457,331, filed Jun. 8, 2009, 10 pages.

Final Office Action dated May 5, 2016, for U.S. Appl. No. 12/457,331, filed Jun. 8, 2009, 11 pages.

Final Office Action dated May 5, 2016, for U.S. Appl. No. 14/311,114, filed Jun. 20, 2014, 13 pages.

Final Office Action dated Oct. 15, 2009, for U.S. Appl. No. 11/239,122, filed Sep. 30, 2005, 13 pages.

Final Office Action dated Aug. 14, 2012, for U.S. Appl. No. 13/037,089, filed Feb. 28, 2011, 14 pages.

Final Office Action dated Sep. 23, 2013, for U.S. Appl. No. 13/037,089, filed Feb. 28, 2011, 14 pages.

Final Office Action dated Mar. 27, 2014, for U.S. Appl. No. 12/457,332, filed Jun. 8, 2009, 11 pages.

Final Office Action dated Jan. 20, 2016, for U.S. Appl. No. 12/457,332, filed Jun. 8, 2009, 10 pages.

Final Office Action dated Apr. 30, 2013, for U.S. Appl. No. 13/168,644, filed Jun. 24, 2011, 10 pages.

Final Office Action dated Sep. 30, 2015, for U.S. Appl. No. 13/168,644, filed Jun. 24, 2011, 16 pages.

Final Office Action dated Aug. 12, 2016, for U.S. Appl. No. 13/168,644, filed Jun. 24, 2011, 18 pages.

Feldman, B. et al. (2000). "Freestyle™: A Small-Volume Electrochemical Glucose Sensor for Home Blood Glucose Testing," *Diabetes Technology and Therapeutics,* 2(2):221-229.

International Search Report dated Jul. 28, 2009, for PCT Patent Application No. PCT/US2009/03441, filed on Jun. 8, 2009, 10 pages.

International Search Report dated Oct. 15, 2014 for PCT Application No. PCT/US2014/043516, filed on Jun. 20, 2014, 2 pages.

International Search Report dated Jan. 16, 2008, for PCT Application No. PCT/US2006/022840, filed on Jun. 13, 2006, 1 page.

International Search Report dated Jul. 28, 2009, for PCT Application No. PCT/US2009/03445, filed on Jun. 8, 2009, 2 pages.

International Search Report dated Nov. 14, 2011, for PCT Application No. PCT/US2011/001132, filed on Jun. 24, 2011, 2 pages.

INTEG. (2000). "LifeGuideÔ Glucose Meter. No Lancets. No Blood," located at <http://www.integonline.com>, last visited May 1, 2000, 10 pages.

Johnson, R.N. et al. (Jan. 1998). "Accuracy of Devices Used for Self-Monitoring of Blood Glucose," *Annals of Clinical Biochemistry* 35(1):68-74.

Johnson, R.N. et al. (Jan. 1999). "Analytical Error of Home Glucose Monitors: A Comparison of 18 Systems," *Annals of Clinical Biochemistry* 36(1):72-79.

Johnson, R.N. et al. (2001). "Error Detection and Measurement In Glucose Monitors," *Clinica Chimica Acta* 307:61-67.

Kumetrix, Inc. (Dec. 1999). "Painless Blood Glucose Monitoring, Courtesy of the Mosquito," *Start-Up* pp. 27-28.

Lee, S-C. (Jun. 1999). "Light Scattering by Closely Spaced Parallel Cylinders Embedded in a Finite Dielectric Slab," *Journal of the Optical Society of America A* 16(6):1350-1361.

McGarraugh, G. et al. (2001). "Physiological Influences on Off-Finger Glucose Testing," *Diabetes Technology & Therapeutics* 3(3):367-376.

McNichols, R.J. et al. (Jan. 2000). "Optical Glucose Sensing in Biological Fluids: An Overview," *Journal of Biomedical Optics,* 5(1):5-16.

Mahler, R.J. et al. (1999). "Clinical Review 102, Type 2 Diabetes Melitus: Update on Diagnosis Pathophysiology, and Treatment," *The Journal of Clinical Endocrinology and Metabolism* 84(4):1165-1171.

Medline Plus. (Jun. 17, 2008)., Medical Encyclopedia, Monitor Blood Glucose-Series: Part 1-4, 6 pages.

Neeley, W.E. et al. (1981). "An Instrument for Digital Matrix Photometry," *Clinical Chemistry* 27(10):1665-1668.

Neeley, W.E. (1983). "Reflectance Digital Matrix Photometry," *Clinical Chemistry* 29(6):1038-1041.

Neeley, W.E. (1983). "Multilayer Film Analysis for Glucose in 1-mL Samples of Plasma," *Clinical Chemistry* 29(12):2103-2105.

Neeley, W.E. (1988). "A Reflectance Photometer with a Square Photodiode Array Detector for Use on Multilayer Dry-Film Slides," *Clinical Chemistry* 34(11):2367-2370.

Non-Final Office Action dated Nov. 23, 2011, for U.S. Appl. No. 12/457,331, filed Jun. 8, 2009, 6 pages.

Non-Final Office Action dated Jun. 13, 2014, for U.S. Appl. No. 12/457,331, filed Jun. 8, 2009, 8 pages.

Non-Final Office Action dated Jul. 8, 2015, for U.S. Appl. No. 12/457,331, filed Jun. 8, 2009, 13 pages.

Non-Final Office Action dated Mar. 19, 2009, for U.S. Appl. No. 11/239,122, filed Sep. 30, 2005, 15 pages.

Non-Final Office Action dated Sep. 1, 2010, for U.S. Appl. No. 11/239,122, filed Sep. 30, 2005, 15 pages.

Non-Final Office Action dated Aug. 19, 2015, for U.S. Appl. No. 14/311,114, filed Jun. 20, 2014, 15 pages.

Non-Final Office Action dated Sep. 13, 2011, for U.S. Appl. No. 13/037,089, filed Feb. 28, 2011, 14 pages.

Non-Final Office Action dated Feb. 28, 2013, for U.S. Appl. No. 13/037,089, filed Feb. 28, 2011, 12 pages.

Non-Final Office Action dated Apr. 10, 2014, for U.S. Appl. No. 13/037,089, filed Feb. 28, 2011, 14 pages.

Non-Final Office Action dated May 29, 2015, for U.S. Appl. No. 14/614,177, filed Feb. 4, 2015, 13 pages.

Non-Final Office Action dated Mar. 2, 2012, for U.S. Appl. No. 12/457,332, filed Jun. 8, 2009, 7 pages.

Non-Final Office Action dated May 30, 2013, for U.S. Appl. No. 12/457,332, filed Jun. 8, 2009, 7 pages.

Non-Final Office Action dated Jun. 22, 2012, for U.S. Appl. No. 13/168,644, filed Jun. 24, 2011, 8 pages.

Non-Final Office Action dated Jan. 13, 2015, for U.S. Appl. No. 13/168,644, filed Jun. 24, 2011, 12 pages.

Non-Final Office Action dated Jun. 25, 2015, for U.S. Appl. No. 12/457,332, filed Jun. 8, 2009, 7 pages.

Notice of Allowance dated Sep. 18, 2014, for U.S. Appl. No. 13/037,089, filed Feb. 28, 2011, 9 pages.—(7.01).

Notice of Allowance dated Feb. 16, 2016, for U.S. Appl. No. 14/614,177, filed Feb. 4, 2015, 7 pages.

Notice of Allowance dated Jan. 26, 2017, for U.S. Appl. No. 12/457,331, filed Jun. 8, 2009, 7 pages.

Otto, E. et al. (2000). "An Intelligent Diabetes Software Prototype: Predicting Blood Glucose Levels and Recommending Regimen Changes," *Diabetes Technology and Therapeutics* 2(4):569-576.

Pfohl, M. et al. (2000). "Spot Glucose Measurement in Epidermal Interstitial Fluid—An Alternative to Capillary Blood Glucose Estimation," *Experimental and Clinical Endocrinology & Diabetes* 108(1):1-4.

Princen, H.M. (May 1969). "Capillary Phenomena in Assemblies of Parallel Cylinders, I. Capillary Rise Between Two Cylinders," *Journal of Colloid and Interface Science* 30(1):69-75.

(56) References Cited

OTHER PUBLICATIONS

Princen, H.M. (Jul. 1969). "Capillary Phenomena in Assemblies of Parallel Cylinders, II. Capillary Rise in Systems with More Than Two Cylinders," *Journal of Colloid and Interface Science* 30(3):359-371.
Rebrin, K. et al. (Sep. 1999). "Subcutaneous Glucose Predicts Plasma Glucose Independent of Insulin: Implications for Continuous Monitoring," *American Journal of Physiology* 277(3):E561-E571.
Rosen, S. (1999). "Road to New-Age Glucose Monitoring Still Rocky," *Diagnostic Insight*, pp. 4-5, 12-13, 16.
Smart, W.H. et al. (2000). "The Use of Silicon Microfabrication Technology in Painless Glucose Monitoring, "*Diabetes Technology & Therapeutics* 2(4):549-559.
Sonntag, O. (1993). Ektachem. Dry Chemistry, Analysis With Carrier-Bound Reagents, Elsevier Science Publishers, 57 pages.
Spielman, A. et al. (2001). *Mosquito: A Natural History of Our Most Persistent and Deadly Foe*, First Edition, Hyperion, New York, NY, 3 pages. (Table of Contents Only).
Straub F.B. (Mar. 1939). "Isolation and Properties of a flavoprotien from Heart Muscle Tissue", Biochemical Journal 33: 787-792.
Svedman, C. et al. (Apr. 1999). "Skin Mini-Erosion Technique for Monitoring Metabolites in Interstitial Fluid: Its Feasibility Demonstrated by OGTT Results in Diabetic and Non-Diabetic Subjects," *Scand. J. Clin. Lab. Invest.* 59(2):115-123.
Tietz, N.W. (1986).Textbook of Clinical Chemistry, W. B. Saunders Company, pp. 1533 and 1556.
Trinder, P. (1969). "Determination of Glucose in Blood Using Glucose Oxidase with an Alternate Oxygen Acceptor," *Annals of Clinical Biochemistry* 6:24-28.
U.S. Precision Lens, Inc. (1983).The Handbook of Plastic Optics.
Written Opinion of the International Searching Authority dated Jul. 28, 2009, for PCT Application No. PCT/US2009/03441, filed on Jun. 8, 2009, 2 pages.
Written Opinion of the International Searching Authority dated Oct. 15, 2014 for PCT Application No. PCT/US2014/043516, filed on Jun. 20, 2014, 5 pages.
Written Opinion of the International Searching Authority dated Jan. 16, 2008, for PCT Application No. PCT/US2006/022840, filed on Jun. 13, 2006, 3 pages.
Written Opinion of the International Searching Authority dated Jul. 28, 2009, for PCT Application No. PCT/US2009/03445, filed on Jun. 8, 2009, 4 pages.
Written Opinion dated Nov. 14, 2011, for PCT Application No. PCT/US2011/001132, filed on Jun. 24, 2011, 6 pages.
Yum, S. I. et al. (Nov. 1, 1999). "Capillary Blood Sampling for Self-Monitoring of Blood Glucose," *Diabetes Technology & Therapeutics*, 1(1):29-37.
Notice of Allowance dated Aug. 18, 2017, for U.S. Appl. No. 13/566,886, filed Aug. 3, 2012, 10 pages.
Non-Final Office Action dated Mar. 21, 2017, for U.S. Appl. No. 15/177,041, filed Jun. 8, 2016, 11 pages.
Non-Final Office Action dated Dec. 16, 2016, for U.S. Appl. No. 13/566,886, filed Aug. 3, 2012, 11 pages.
Extended European Search Report dated Nov. 8, 2016 by the European Patent Office for Application No. 16167087.2, filed Aug. 3, 2012, 7 pages.
Final Office Action dated Nov. 29, 2017, for U.S. Appl. No. 15/177,041, filed Jun. 8, 2016, 13 pages.
International Search Report dated Oct. 19, 2012 for PCT Application No. PCT/US2012/049629, filed on Aug. 3, 2012, 4 pages.
Non-Final Office Action dated Mar. 20, 2017, by The United States Patent and Trademark Office for U.S. Appl. No. 15/191,434, filed Jun. 23, 2016, 20 pages.
Non-Final Office Action dated Jun. 20, 2017, for U.S. Appl. No. 15/191,434, filed Jun. 23, 2016, 20 pages.
Final Office Action dated Dec. 20, 2017, for U.S. Appl. No. 15/191,434, filed Jun. 23, 2016, 21 pages.
Extended European Search Report dated Jan. 20, 2017, for EP Application No. 14 813 126.1, filed Jun. 20, 2014, 8 pages.
Non-Final Office Action dated Mar. 8, 2017, for U.S. Appl. No. 14/311,114, filed Jun. 20, 2014, 24 pages.
Final Office Action dated Nov. 13, 2017, for U.S. Appl. No. 14/311,114, filed Jun. 20, 2014, 15 pages.
Final Office Action dated Feb. 8, 2017, for U.S. Appl. No. 12/457,332, filed Jun. 8, 2009, 11 pages.
Final Office Action dated Mar. 28, 2018, for U.S. Appl. No. 12/457,332, filed Jun. 8, 2009, 13 pages.
Final Office Action dated Sep. 21, 2017, for U.S. Appl. No. 13/168,644, filed Jun. 24, 2011, 14 pages.
Notice of Allowance dated Jul. 20, 2018, for U.S. Appl. No. 15/177,041, filed Jun. 8, 2016, 11 pages.
Non-Final Office Action dated Aug. 10, 2018, for U.S. Appl. No. 14/311,114, filed Jun. 20, 2014, 15 pages.
Non-Final Office Action dated Aug. 15, 2018, for U.S. Appl. No. 15/191,434, filed Jun. 23, 2016, 19 pages.
Extended European Search Report dated Jan. 17, 2020, for European Application No. 19187252.2, 12 pages.
Extended European Search Report dated Nov. 10, 2020 from the European Patent Office for Application No. 20169957.6, filed Aug. 3, 2012, 6 pages.
Khalil, "Non-invasive glucose measurement technologies: an update from 1999 to the dawn of the new millennium," Diabetes Technology & Therapeutics., vol. 6, No. 5, 2004.
Non-Final Office Action dated Nov. 27, 2019, for U.S. Appl. No. 15/697,311, filed Sep. 6, 2017, 7 pages.
Non-Final Office Action dated Apr. 20, 2020, for U.S. Appl. No. 16/159,546, filed Oct. 12, 2018, 8 pages.
Non-Final Office Action dated Aug. 7, 2020, for U.S. Appl. No. 15/697,311, filed Sep. 6, 2017, 10 pages.
Notice of Allowance dated Mar. 4, 2021, for U.S. Appl. No. 15/697,311, filed Sep. 6, 2017, 9 pages.
Final Office Action dated Jul. 14, 2021, for U.S. Appl. No. 16/159,546, filed Oct. 12, 2018, 13 pages.
Non-Final Office Action dated Mar. 27, 2019, for U.S. Appl. No. 12/457,332, filed Jun. 8, 2009, 8 pages.
Notice of Allowance dated May 15, 2019, for U.S. Appl. No. 12/457,332, filed Jun. 8, 2009, 8 pages.
Final Office Action dated Apr. 25, 2019, for U.S. Appl. No. 14/311,114, filed Jun. 20, 2014, 16 pages.
Notice of Allowance dated Feb. 4, 2019, for U.S. Appl. No. 13/168,644, filed Jun. 24, 2011, 9 pages.

\* cited by examiner

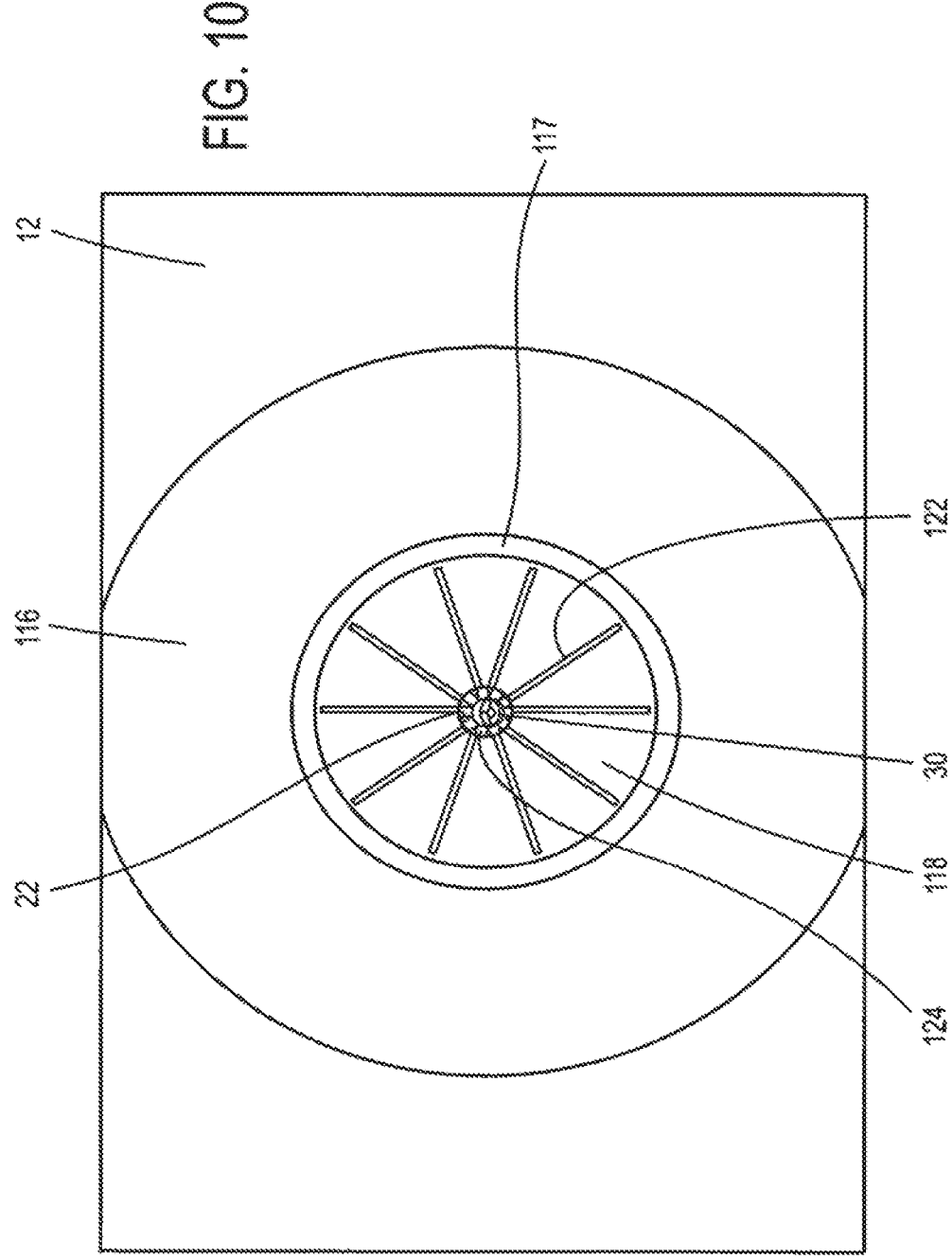

DETECTION METER AND MODE OF OPERATION

CROSS-REFERENCE TO RELATED APPLICATIONS

The present application is a continuation of U.S. patent application Ser. No. 12/457,331, filed Jun. 8, 2009, issued as U.S. Pat. No. 9,636,051 on May 2, 2017, the disclosure of which is hereby incorporated by reference in its entirety, and which claims priority to U.S. Patent Application No. 61/129,149, filed Jun. 6, 2008.

FIELD

The present invention relates to devices, arrangements and methods involving measurements of the presence or concentration of an analyte contained in a sample of body fluid.

BACKGROUND

In this specification where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

According to the American Diabetes Association, diabetes is the fifth-deadliest disease in the United States. Since 1987 the death rate due to diabetes has increased by 45 percent. There are an estimated 20.8 million children and adults in the United States, or 7% of the population, who have diabetes. The total annual economic cost of diabetes in 2007 was estimated to be $174 billion. This is an increase of $42 billion since 2002. This 32% increase means the dollar amount has risen over $8 billion each year.

A critical component in managing diabetes is frequent blood glucose monitoring. Currently, a number of systems exist for self-monitoring by the patient. Most fluid analysis systems, such as systems for analyzing a sample of blood for glucose content, comprise multiple separate components such as separate lancing, transport, and quantification portions. These systems are bulky, and often confusing and complicated for the user.

As a result, certain efforts have been made to develop an "integrated device" that combines the steps and mechanisms for acquiring a sample body fluid, transporting the body fluid to a measurement device, and quantifying the level of analyte contained in the sample body fluid all in a single device. Examples of such devices are illustrated in U.S. Pat. Nos. 6,540,675 and 7,004,928. Although such devices are designed to reliably obtain an adequate sample volume from the user, occasionally, for a number of different reasons, the device will be unable to successfully collect and transport an adequate sample volume for analysis on a first attempt. Devices such as those described above include a skin-penetration member, such as a needle which is driven into the surface of the skin of the user. Once the skin-penetration member has been triggered or activated, such devices typically lack the ability to be "re-cocked" so that the same skin-penetration member can be used again to pierce the surface of the skin. When an inadequate sample volume is collected and transported as a result of the initial wound creation, that particular test cannot proceed. Thus, the test is "wasted." The user must perform a new test using a fresh skin-penetration member and quantification member. This can increase the costs to the user associated with monitoring the analyte or glucose levels. Moreover, the inability to salvage a successful test from a single wound means that the user will often create a separate wound at a new sampling site, or be forced to cause further damage to the existing wound in order to collect and transport an adequate sample volume for analysis. This obviously increases the pain and frustration experienced by the user, which is counterproductive to the goal of encouraging the user to frequently and systematically monitor their analyte or glucose levels.

Therefore, there is a need in the art for providing body fluid sampling and analysis techniques and devices which offer the user greater flexibility in the collection of an adequate sample volume to present to the device for analysis.

SUMMARY

According to the present invention, there are provided constructions, arrangements and techniques that may address one or more of the above-mentioned objectives. However, the present invention is not limited to the context of blood sampling performed for the purposes of monitoring glucose concentration. Numerous alternative applications or uses for the concepts described herein are contemplated.

According to certain aspects of the present invention, there are provided devices, constructions, arrangements and techniques that may optionally provide one or more of the following benefits or advantages: notifying the user that an inadequate sample volume has been collected or transported, and providing the user with an opportunity to re-apply a sample of body fluid in order to provide the necessary sample volume for analysis.

As used herein "digital" means fingers or toes, and encompasses lancing sites on the dorsal or palm side of the distal finger tips.

As used herein, "body fluid" encompasses whole blood, intestinal fluid, and mixtures thereof, as well as urine, saliva and other fluids contained in the body.

As used herein "integrated device" or "integrated meter" means a device or meter that includes all components necessary to perform sampling of body fluid, transport of body fluid, quantification of an analyte, and display of the amount of analyte contained in the sample of body fluid.

It is to be understood that reference herein to first, second, third and fourth components (etc.) does not limit the present invention to embodiments where each of these components is physically separable from one another. For example, a single physical element of the invention may perform the functions of more than one of the claimed first, second, third or fourth components. Conversely, a plurality of separate physical elements working together may perform the functions of one of the claimed first, second, third or fourth components. Similarly, reference to first, second (etc.) method steps does not limit the invention to only separate steps. According to the invention, a single method step may satisfy multiple steps described herein. Conversely, a plurality of method steps could, in combination, constitute a single method step recited herein. In addition, the steps of the method are not necessarily limited to the order in which they are described or claimed herein. The term "and" is generally intended to include the alternative of the terms appearing on either side thereof, and does not generally require the presence of both.

According to one aspect, the present invention is directed to a method of performing an assay to determine the presence or concentration of an analyte contained in a sample of body fluid by using a device comprising at least one analyte quantification member and a sensor associated therewith, the method comprising: applying a first sample to the analyte quantification member; detecting the presence or absence of an adequate sample volume; wherein upon detection of the absence of an adequate sample volume, initiating a finite timed period, and signaling the user to introduce a second sample of body fluid to the analyte quantification member.

According to another aspect, the present invention is directed to a device for performing an assay to determine the presence or concentration of an analyte contained in a sample of body fluid, the device comprising: at least one analyte quantification member; at least one passageway in fluid communication with the at least one analyte quantification member; a sensor constructed and arranged to detect the presence or absence of an adequate sample volume applied to the at least one analyte quantification member; and a controller in signal communication with the sensor, the controller is configured and arranged such that upon detection of the absence of an adequate sample volume, the controller initiates a finite timed period and signals the user to introduce another sample of body fluid into the at least one passageway.

A device for collecting a sample of body fluid, the device comprising: a skin interface member and a skin penetration member, wherein at least one of the skin interface member and the skin penetration member comprises a guide element configured to direct the flow of body fluid in a desired direction toward a desired location.

BRIEF DESCRIPTION OF THE DRAWING FIGURES

The following description of preferred embodiments can be read in connection with the accompanying drawings in which like numerals designate like elements and in which:

FIG. 10 is a top perspective view of the arrangement of FIG. 9.

DETAILED DESCRIPTION

According to a first aspect of the present invention, there are provided techniques for performing an assay to determine the presence and/or concentration of an analyte contained in a sample of body fluid. For example, according to the present invention, the techniques described herein can be used to analyze a sample of body fluid to quantify the amount of an analyte (e.g., glucose, bilirubin, alcohol, controlled substances, toxins, hormones, proteins, etc.) contained therein.

Figure 1:
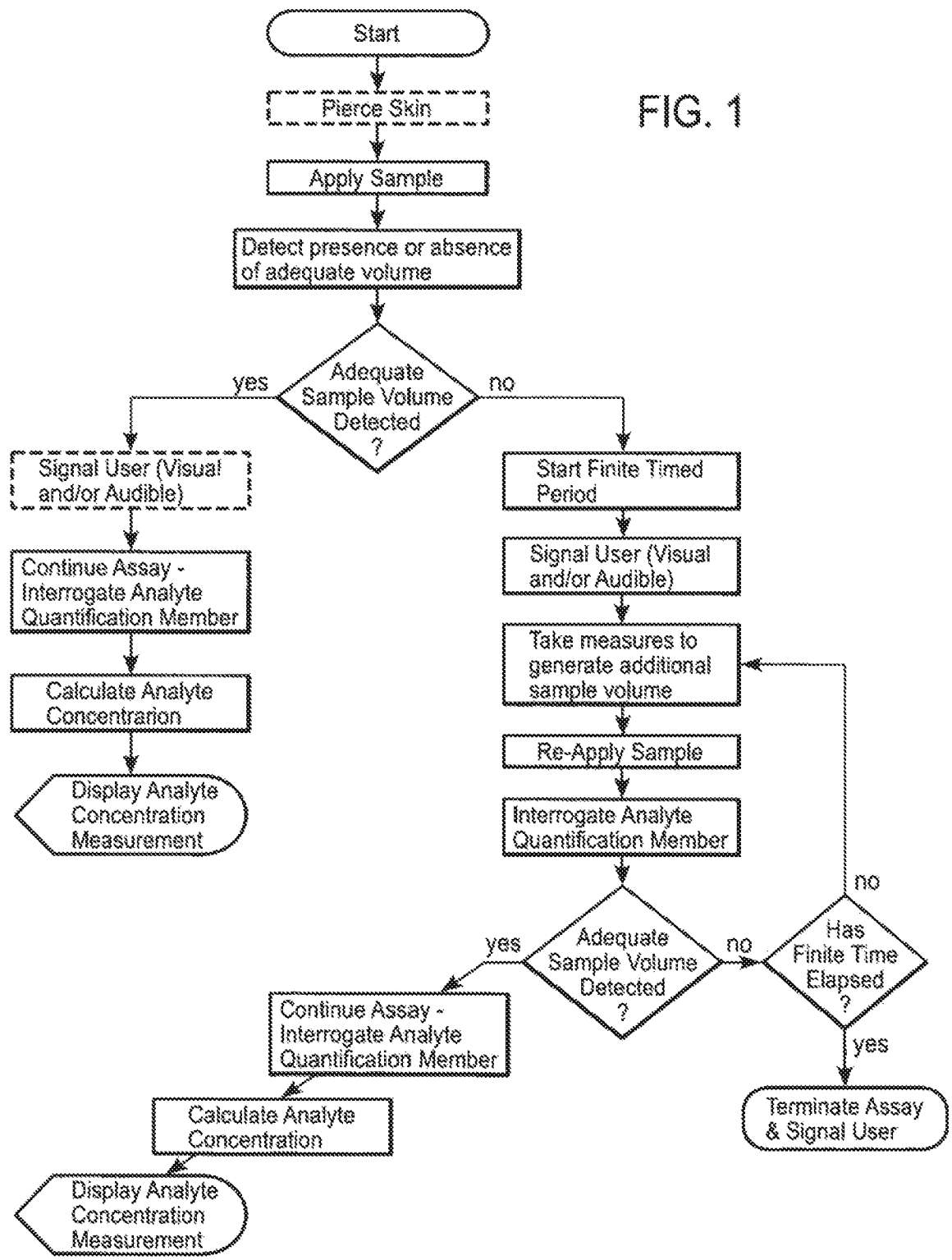
FIG. 1 is a flowchart illustrating certain methods performed according to the principles of the present invention.

Exemplary methods performed according to the principles of the present invention are illustrated by the flowchart appearing in FIG. 1. The method begins with the production of a sample of body fluid. The manner in which the sample of body fluid is produced or collected is not critical to the practice of the techniques of the present invention. For example, in a situation where the methods or techniques of the present invention are practiced in the context of patient self-monitoring of blood glucose levels, or taking a blood glucose level measurements in a clinical setting, a small volume of blood can be produced by piercing the skin to create a wound at a sampling site from which the body fluid can be expressed. The sampling site that is chosen may include a digital skin surface, or an alternative sampling site such as the forearms, thighs, and the like. Thus, as indicated by the broken-line process box appearing in FIG. 1, the step of piercing the skin is optional within the context of the methods and techniques of the present invention. When practiced, the skin can be pierced by any suitable device or technique. Suitable devices and techniques include lancets, hollow needles, a burst of fluid pressure, concentrated energy (e.g., laser), and the like.

Once a sample of body fluid has been produced, it is then applied to at least one analyte quantification member. Any suitable form of analyte quantification member may be utilized. Thus, for example, the analyte quantification member can be either electrochemical or photometric in nature. According to one particular illustrative, non-limiting embodiment, the least one analyte quantification member may comprise an assay pad containing a chemical reagent which is formulated such that a color change is produced upon reaction with a target analyte, as known per se to those skilled in the art.

At least one sensor is utilized to for purpose of detecting the presence or absence of an adequate sample volume. Any suitable sensor construction or arrangement may be utilized to detect, calculate and/or estimate sample volume. Thus, for example, the sensor may be either electrochemical or photometric in nature. The sensor may be separate and not otherwise associated with the least one analyte quantification member. According to one illustrative, non-limiting example, the sensor may comprise a flow sensor which detects, and possibly quantifies, the flow of body fluid to the least one analyte quantification member. Alternatively, the least one sensor may comprise an electrochemical or optical sensor that interrogates the at least one analyte quantification member to detect the presence of the sample of body fluid, and to calculate and/or estimate the volume of the sample. According to one non-limiting example, when the at least one analyte quantification member comprises an assay pad containing a chemical reagent which changes color upon exposure to the target analyte, an optical sensor can be used to interrogate the at least one analyte quantification member and detect this color change in those areas of the assay pad which have been contacted by the body fluid sample containing the target analyte. Examples of suitable sensors which can be utilized in this manner include, but are not limited to, CCD and CMOS type sensors. The sensor can also determine or estimate the area of the assay pad which has changed color due to contact with the sample of body fluid. This area can then be used by supporting electronics to calculate and/or estimate the volume of body fluid applied to the at least one analyte quantification member. A detailed explanation of such a calculation or estimation is contained in U.S. Pat. No. 7,052,652, the entire contents of which are incorporated herein by reference.

If the sensor determines that an adequate volume of body fluid has been introduced to the least one analyte quantification member within an acceptable time frame, the assay continues with the calculation of the presence and/or amount of analyte contained within the sample of body fluid. Optionally, the user may be signaled by the device or meter that an adequate volume of sample has been detected. Any suitable audible and/or visual signal may be generated and used for this purpose. Thus, for example, a message containing alphanumeric characters and/or symbols can be generated on a display. Alternatively, a "green light" or other visual cue may be generated by any portion of a meter or device. In addition, an audible signal, such as a spoken message or audible cue may be generated instead of, or in addition to, the above mentioned visual signal. Again, any suitable technique can be utilized to detect the analyte and/or calculate its concentration. Thus, for example, both electrochemical and photometric techniques can be utilized. According to one non-limiting example, when at least one analyte quantification member comprises an assay pad containing a chemical reagent which produces a color change upon reaction with the target analyte, an optical sensor can be utilized to interrogate the at least one analyte quantification member, subsequent to the detection of an adequate sample volume, to detect to change in color produced by reaction between the target analyte and the chemical reagent. This change in color can then be correlated with a particular analyte concentration. This type of photometric analysis is known per se to those skilled in the art. Once a calculation of the amount of target analyte contained in the sample of body fluid has been performed, the results of the calculation can then be displayed for the user. Any suitable arrangement of conventional electronics and/or software components, which may include a controller, central processing unit (CPU), memory components, electrical connections, and the like, can be utilized in conjunction with the above-mentioned sensor and at least one analyte quantification member to perform the necessary calculations, and generate visual and/or audible signals.

If the sensor determines that an inadequate volume of body fluid has been introduced to the least one analyte quantification member within the above-mentioned time frame, according to the present invention steps are then taken in an attempt to salvage the assay. A second finite time period can be initiated which allows the user time to take additional steps to supply an adequate volume of body fluid. This second finite time period may comprise any suitable amount of time. According to illustrative non-limiting examples, the second finite time period can be less than one minute, or 45 seconds or less. The user may also be provided with a visual and/or audible signal to indicate that additional steps are necessary in order to apply an adequate volume of body fluid to perform the assay. This signaling may take place prior to the start of the finite time period, concurrently with the start of the finite time period, or subsequent to the start of the finite time period. Any suitable visual and/or audible signal may be utilized, as discussed above.

In response to receiving the signal to take additional steps to produce an adequate sample of body fluid, and present it to the least one analyte quantification member, any additional steps which could produce such additional sample volume may be undertaken. According to one non-limiting example, when the sample of body fluid has been produced by piercing the skin to create a wound from which body fluid can be expressed, the additional steps taken to increase the volume of the sample body fluid may include having the user apply a manual "milking" action in the vicinity of the wound. This is achieved by alternately squeezing and releasing the skin in the vicinity of the wound to express additional body fluid therefrom. This technique is well-known by people who have diabetes and regularly monitor their blood glucose levels, and is often successful in expressing a sufficient quantity of body fluid in order to perform an assay to determine blood glucose concentration.

Alternatively, some techniques and devices for producing a sample of body fluid by piercing the skin utilize some form of catalyst to increase the amount of body fluid expressed from the wound created by piercing the skin. Suitable catalysts include heat, pressure, vacuum, vibration, and topical drugs. These catalysts may be applied before, during, or after piercing the skin, or a combination of these times. According to the present invention, if an inadequate quantity of body fluid is produced after piercing the skin, upon receiving the above-mentioned signal that an inadequate sample body fluid has been detected, the user may then be instructed, or decide on their own, to administer a catalyst in the vicinity of the wound in an attempt to increase the amount of body fluid expressed therefrom, regardless of whether or not a catalyst was utilized in connection with the initial wound creation and body fluid sample extraction. Any suitable arrangement of conventional electronics and/or software components, which may include a controller, central processing unit (CPU), memory components, electrical connections, display components, and the like, can be utilized to generate visual and/or audible signals, which may include specific instructions with respect to the reapplication of a catalyst. It is comprehended within the scope of the present invention that the user may make one, or multiple attempts, to produce an adequate volume of body fluid within the second predetermined time period. If more than one attempt is made, the same technique (e.g., milking or application of a catalyst) can be repeated. Alternatively, the multiple attempts can comprise a combination of different techniques for expressing an adequate sample volume. By way of nonlimiting example, a user could attempt to milk additional body fluid from the wound one or more times, and if unsuccessful, then apply a catalyst to the wound site one or more times, all within the predetermined second time period. This technique or functionality is represented in the flow diagram appearing in FIG. 1. It should be understood that any of the techniques or methods described herein may be practiced so as to include this technique or functionality. Similarly, any device or arrangement described herein may also be constructed, or utilized, in a manner consistent with this technique or functionality.

If the sensor determines that an inadequate volume of body fluid has been introduced to the least one analyte quantification member within the above-mentioned second finite time period, the assay may be terminated. An appropriate signal may be generated to indicate to the user that the assay has been terminated, or the testing event has failed.

If the sensor determines that an adequate volume of body fluid has been introduced to the least one analyte quantification member within the above-mentioned second time period, the assay can then continue. Thus, the assay continues with the calculation of the presence and/or amount of analyte contained within the sample of body fluid. Again, any suitable technique can be utilized to detect the analyte and/or calculate its concentration. Thus, for example, both electrochemical and photometric techniques can be utilized, such as those non-limiting examples already discussed above. Once the analyte presence and/or concentration has been calculated, the results may be presented to the user by one or more of visual and audible signals.

Since body fluid such as blood may naturally attempt to coagulate upon exposure to the environment, it may be advantageous to take some measures which will permit the continued flow of body fluid after a certain period of time has elapsed. Thus, for example, a sample of body fluid may be applied to the at least one analyte quantification member which proves to have an inadequate volume. Upon detection of this inadequate volume, and with the optional signaling to the user of this condition, the additional steps discussed above may be taken in order to attempt to salvage the test. As mentioned above, these additional steps may take some period of time to complete. During the period of time which is elapsed since the first application of body fluid, the above-mentioned coagulation effect may impede or completely block the flow of additional sample which is subsequently applied. Therefore, according to the principles of the present invention, steps may be taken to prevent coagulation of the body fluid. One illustrative, non-limiting example would be to apply an anticoagulant material, at least partially, to one or more components or members within which the body fluid comes into contact. Examples of suitable anticoagulant materials may include, but are not limited to, aspirin, heparin and Coumadin®.

According to further aspects of the present invention, there are provided arrangements and/or devices which are constructed and arranged to have a more flexible mode of operation and that may achieve one or more of the advantages associated with the principles of the present invention. It is to be understood that any of the arrangements and/or devices described herein may be utilized to practice the techniques or methods of the present invention which have been previously described.

Figure 2:
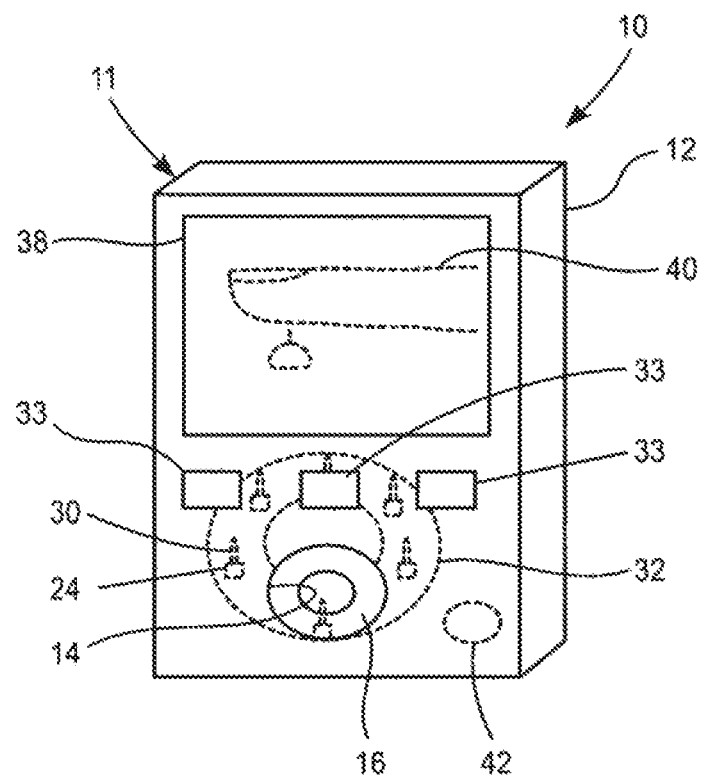
FIG. 2 is a front perspective view of a device formed according to other aspects of the present invention.
Figure 3:
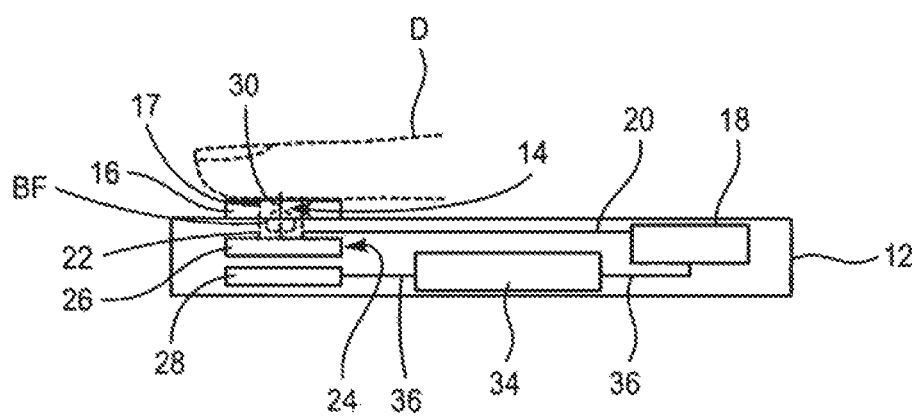
FIG. 3 is a cut away side view of the device of FIG. 2.

One embodiment of an arrangement 10 of the type described above may be in the form of a device, as illustrated in FIGS. 2-3. As illustrated therein, the arrangement 10 may optionally be in the form of an integrated meter or device 11. It should be understood that any of the methods, arrangements and devices described herein may be practiced with an integrated meter, which may have one or more of the features of the integrated device 11 of the illustrated embodiment. However, it should be made clear that the present invention is necessarily not so limited. The methods, arrangements and devices of the present invention are applicable to a number of different devices and systems, such as simple lancing devices, meters that lack any sample creation mechanisms, multiple component systems, and the like. Similarly, the arrangements and devices described herein can be constructed and arranged to function in accordance with the methods of the present invention, but are not necessarily so limited.

The methods, arrangements and devices described herein may be used at, or applied to, a skin surface of a user at a suitable sampling site. One suitable sampling site is on a digit D. However, the methods, arrangements and devices are not necessarily so limited. For example, the methods, arrangements and devices described herein may be used or applied to any skin surface at any suitable sampling site which may include alternative sampling sites such as the forearm, thigh, etc.

According to the embodiment illustrated in FIGS. 2-3, the arrangement 10 or meter 11 includes a housing 12. The housing 12 may have any suitable shape or configuration, and is not limited to the shape and configuration illustrated. For example, the housing 12 be contoured such that it is easily grasped by the hand of the user. The housing 12 can be constructed of any suitable material. For example, the housing 12 may be constructed of a polymeric or metallic material. The housing 12 may comprise an opening 14 disposed therein. A skin interface member 16 may be disposed in the opening 14 and attached to the housing 12. The skin interface member 16 can be provided with any suitable construction, or formed from any suitable materials. For example, the skin interface member can be formed from an elastomer, silicone rubber, soft plastic, or combination of materials with different properties. A number of alternative skin interface member constructions are contemplated, as will be further described herein.

The arrangement 10 or device 11 may further optionally include a catalyst to assist in the sample acquisition process by enhancing or facilitating perfusion of body fluid at a sampling site. At least one of several catalysts may be utilized or included in the arrangement of the present invention. Possible catalysts include, heat, pressure, vacuum, vibration, and topical drugs (which induce vasodilatation and increases the blood or body fluid available at the lancing site). These catalysts may be applied before, during, after piercing of the skin, or in a combination with some or all three times, to facilitate expression of sufficient quantity of body fluid BF for determination of the concentration of an analyte (e.g., glucose) contained therein. According to the principles of the present invention, one or more of the above-described catalysts can be used in combination with each other, either concurrently or sequentially.

According to certain embodiments, a light vacuum (e.g., 3-8 in. Hg) is applied to the surface of the skin at the sampling site via opening 14, either before, during, and/or after piercing the skin. Several embodiments for applying vacuum to the wound site are contemplated. One embodiment uses a pump 18 to apply vacuum to the area of the skin via the opening 14. The pump 18 is in communication with the opening via any suitable mechanism, such as the illustrated fluid communication line 20. Alternative embodiments include using individually packaged vacuum chambers to apply vacuum, or using a syringe like mechanism to apply vacuum.

The arrangement 10 or device 11 may further comprise any suitable form of analyte quantification member 24. For example, the analyte quantification member 24 can be either electrochemical or photometric in nature. According to one particular illustrative, non-limiting embodiment, the least one analyte quantification member 24 may comprise an assay pad 26 containing a chemical reagent which is formulated such that the color changes produced upon reaction with a target analyte, as known per se to those skilled in the art. A sample of body fluid BF may be introduced to the analyte quantification member by any suitable construction or technique. For example, the sample of body fluid BF may be introduced via the opening 14 and/or passageway 22.

At least one sensor 28 may be provided in conjunction with the at least one analyte quantification member 24. Any suitable sensor 28 construction or arrangement may be provided to interrogate the at least one analyte quantification member 24. The sensor may be integrated with the analyte quantification member 24, or it may be separate and not otherwise associated therewith. For example, the analyte quantification member 24 can be analyzed by a sensor 28 that forms part of the arrangement 10 or device 11. Alternatively, the analyte quantification member 24 is removed or separate from the arrangement 10 or device 11, and inserted into an electrochemical or photometric meter.

The least one sensor 28 may comprise an electrochemical or optical sensor that interrogates the at least one analyte quantification member 24 to detect the presence of the sample of body fluid, and/or to calculate or estimate the volume of the sample. According to one non-limiting example, when the at least one analyte quantification member comprises an assay pad 26 containing a chemical reagent which changes color upon exposure to the target analyte, an optical sensor 28 can be used to interrogate the at least one analyte quantification member 24 and detect this color change in those areas of the assay pad 26 which have been contacted by the body fluid sample BF containing the target analyte. Examples of suitable optical sensors which can be utilized in this manner include, but are not limited to, CCD and CMOS type sensors. The sensor 28 can also determine or estimate the area of the assay pad which has changed color due to contact with the sample of body fluid. This area can then be used to calculate and/or estimate of the volume of body fluid applied to the at least one analyte quantification member. A detailed explanation of such a calculation or estimation is contained in U.S. Pat. No. 7,052,652, the entire contents of which are incorporated herein by reference.

The arrangement 10 or device 11 may further includes at least one skin-penetration member 30. The at least one skin-penetration member 30 can take any suitable form. For example, the at least one skin-penetration member can comprise a solid lancet or a hollow needle. Conventional arrangements often require separate mechanisms for drawing a sample of blood to the surface of the skin and for transporting the sample to a reaction chamber. The arrangements of the present invention can optionally include a skin-penetration member 30 in the form of a hollow needle having an inner lumen to both create a wound opening and transport the sample, thereby greatly simplifying and improving the effectiveness of the arrangement 10 or device 11.

According to one optional embodiment, the skin-penetration member(s) 30 can be in the form of a so-called "microneedle." As the name implies, microneedles are characterizable by their relatively small outer diameters. For example, a microneedle, as the term is utilized herein, may encompass a skin-penetration member having an outside diameter which is on the order of 40-200 µm. When the microneedle is hollow and comprises an inner lumen, the inside diameter can vary. For example, having an inside diameter on the order of 25-160 µm. Needles are also characterizable in the art by reference to the "gage." By way of illustration, and consistent with the above description, microneedles having a gage ranging from 26-36 are clearly comprehended by the present invention. Certain advantages may be gleaned from the use of such microneedles as the skin-penetration member. In particular, due to their small size, the size of the wound left upon entry into the skin is relatively small, thereby minimizing the pain associated with such needle insertions and allowing for a quicker healing process. However, the present invention is certainly not limited to the use of such microneedles. Thus, for example, according to one possible alternative embodiment, the skin penetration member(s) comprise hollow needles having a gage of about 20-25, or comprising hollow needles having an inner diameter of about 0.007 inches and an outer diameter of about 0.020 inches.

The at least one skin-penetration member 30 can be formed of any suitable material, such as metal, plastic, glass, etc. Optionally, the at least one skin penetration member can be in fluid communication with an analyte quantification member 24.

The at least one skin-penetration member 30, and/or the analyte quantification member 24 can be attached to an actuation element (not shown), such as a spring. The actuation element drives the at least one skin-penetration member 30 into the skin at the sampling site.

As further illustrated in FIGS. 2-3, the arrangement 10 or device 11 can comprise a plurality of skin penetration members 30 and/or analyte quantification members 24. The plurality of skin penetration members 30 and/or analyte quantification members 24 may optionally be mounted within a removable cartridge 32. Thus, the arrangement 10, particularly when in the form of an integrated device 11, is capable of performing a number of assays on collected body fluid BF samples in a fully self-contained a manner. After a number of assays have been performed which correspond to the number of skin penetration members 30 and analyte quantification members 24, the cartridge 32 can be removed, discarded, and replaced with a new cartridge.

According to certain embodiments of the present invention, the arrangement 10 can operate in an automatic or semi-automatic manner. For example, a user may place the skin interface member 16 over the surface of the skin and when the user is ready to produce a sample of body fluid and/or perform an assay, the user initiates the process by, for example, pressing a button 33, touch screen or other interface device. This can initiate a programmed sequence of events in the device which may include one or more of actuation of a catalyst, and driving the skin-penetration member 30 into the skin. At a predetermined time, the catalyst is deactivated. This mode of operation can be characterized as "semi-automatic" in that sequence of events must be manually initiated by the user.

According to one alternative, the mode of operation can be fully automatic. For example, the user places the skin interface member 16 over the skin at a suitable sampling site. The arrangement 10 or device 11 can be provided with one or more sensor 17 that detect and verify that the skin of the user is properly located over the opening 14 and ready for the sampling procedure to begin. The one or more sensor can comprise any suitable sensor, such as a capacitive touch sensor, a resistive touch sensor a dome switch, or a microswitch. Once this state has been sensed, the device automatically activates a programmed sequence of events in the device which may include one or more of activation of a catalyst, and driving the skin-penetration member 30 into the skin. At a subsequent predetermined time, the catalyst device 14 is deactivated. The catalyst device can be deactivated before, during or after the skin-penetration member is driven into the skin.

An arrangement 10 or device 11 formed according to the principles of the present invention may also include supporting electronics. Thus, for example, the arrangement 10 or device 11 may include a controller 34 which is in signal communication 36 with the sensor 28 and the optional pump 18. The controller 34 may include a central processing unit, memory, control logic (e.g., code), power supply, supporting electronics, and the like, as familiar per se to those skilled in the art. The controller 34 controls the operations of the arrangement 10 or device 11.

The controller 34, in conjunction with one or more of the features of the arrangement 10 or device 11 described herein, may be used to execute one or more of the steps of the methods described above in connection with certain aspects of the present invention. Exemplary body fluid analysis methods which may be performed in conjunction with the above-described arrangement 10 or device 11, but are not necessarily limited thereto, is described as follows.

The manner in which the sample of body fluid is produced or collected is not critical to the practice of the techniques of the present invention. For example, in a situation where the methods or techniques of the present invention are practiced in the context of patient self-monitoring of blood glucose levels, or taking a blood glucose level measurements in a clinical setting, a small volume of blood can be produced by piercing the skin to create a wound at a sampling site from which the body fluid can be expressed. The sampling site that is chosen may include a digital skin surface, or an alternative sampling site such as the forearms, thighs, and the like. Thus, when the arrangement 10 is implemented in the form of an optional integrated device (e.g., 11), the skin can be pierced by the at least one skin-penetration member 30 to create a wound in the surface of the skin from which a sample of body fluid BF can be expressed.

Once a sample of body fluid BF has been produced, it is then applied to at least one analyte quantification member 24 via the opening 14 and/or passageway 22. The sensor 28 may optionally be utilized to for purpose of detecting the presence or absence of an adequate sample volume. According to one non-limiting example, when the at least one analyte quantification member 24 comprises an assay pad 26 containing a chemical reagent which changes color upon exposure to the target analyte, an optical sensor can be used to interrogate the at least one analyte quantification member and detect this color change in those areas of the assay pad 26 which have been contacted by the body fluid sample BF containing the target analyte. This area can then be used by supporting electronics (e.g., controller 34, central processing unit, memory, control logic (e.g., code), power supply, etc.) to calculate and/or estimate of the volume of body fluid applied to the at least one analyte quantification member as previously described herein.

If the sensor 28 determines that an adequate volume of body fluid has been introduced to the least one analyte quantification member within an acceptable time frame, the controller 34 directs the assay to continue with the calculation of the presence and/or amount of analyte contained within the sample of body fluid. When at least one analyte quantification member 24 comprises an assay pad 26 containing a chemical reagent which produces a color change upon reaction with the target analyte, the sensor 28 can be utilized to interrogate the at least one analyte quantification member 24, subsequent to the detection of an adequate sample volume, to detect the change in color produced by reaction between the target analyte and the chemical reagent. This change in color can then be correlated with a particular analyte concentration. This type of photometric analysis is known per se to those skilled in the art. Once a calculation of the amount of target analyte contained in the sample of body fluid has been performed, the results of the calculation can then be visually presented on a display 38, or audibly communicated via a speaker 42, for the user.

If, as a result of the interrogation by the sensor 28, it is determined that an inadequate volume of body fluid BF has been introduced to the least one analyte quantification member 24 within the above-mentioned time frame, according to the present invention steps are then taken in an attempt to salvage the assay. A second finite time period can be initiated by the controller 34 which allows the user time to take additional steps to apply an adequate volume of body fluid. This second finite time period may comprise any suitable amount of time. According to illustrative non-limiting examples, the second finite time period can be less than one minute, or 45 seconds or less. The controller 34 may also provide the user with a visual signal 40 on the display 38, and/or audible signal via speaker 42, to indicate that additional steps are necessary in order to apply an adequate volume of body fluid to perform the assay. This signaling may take place prior to the start of the finite time period, concurrently with the start of the finite time period, or subsequent to the start of the finite time period.

In response to receiving the signal to take additional steps to produce an adequate sample of body fluid, and present it to the at least one analyte quantification member 24, any additional steps which could produce such additional sample volume may be undertaken. According to one non-limiting example, when the sample of body fluid has been produced by piercing the skin to create a wound from which body fluid can be expressed, the additional steps taken to increase the volume of the sample body fluid may include having the user or apply a manual "milking" action in the vicinity of the wound. This is achieved by alternately squeezing and releasing the skin in the vicinity of the wound to express additional body fluid therefrom. This technique is well-known by people who have diabetes and regularly monitor their blood glucose levels, and is often successful in expressing a sufficient quantity of body fluid in order to perform an assay to determine blood glucose concentration. Once additional sample has been milked from the wound, the additional or "second" sample is applied to the analyte quantification member 24 via the opening 14 and/or passageway 22.

Alternatively, if an inadequate quantity of body fluid BF is produced after piercing the skin in conjunction with a first application of a catalyst, upon receiving the above-mentioned signal that an inadequate sample body fluid has been detected, the user may then be instructed via the aforementioned signaling, or decide on their own, to administer a catalyst of in the vicinity of the wound in an attempt to increase the amount of body fluid expressed therefrom regardless of whether a catalyst was used in conjunction with initial wound creation and body fluid sample extraction. Thus, for example, when a vacuum catalyst is utilized the user may be instructed, or decide on their own, to place the skin interface member 16 over the wound and reapply the vacuum catalyst. The catalyst can be applied in any suitable manner. Thus, after placing the skin interface member 16 over the wound, the user can initiate the catalyst by pressing a button 33, touchscreen or any other suitable interface device. Alternatively, the application of the catalyst may be automatically initiated through sensing that the skin is properly located over the skin interface member 16, as described above.

If the sensor 28 determines that an inadequate volume of body fluid BF has been introduced to the least one analyte quantification member 24 within the above-mentioned second finite time frame, the assay may be terminated. An appropriate signal may be generated on the display 38 or via the speaker 42 to indicate to the user that the assay has been terminated, or the testing event has failed.

If the sensor 28 determines that an adequate volume of body fluid has been introduced to the least one analyte quantification member 24 within the above-mentioned second time frame, the assay can then continue. Thus, the assay continues with the calculation of the presence and/or amount of analyte contained within the sample of body fluid in the manner described above. Once the analyte presence and/or concentration has been calculated, the results may be presented to the user through one or more of visual and audible signals via the display 38 or speaker 42.

Since body fluid such as blood may naturally attempt to coagulate upon exposure to the environment, it may be advantageous to take some measures which will permit the continued flow of body fluid after a certain period of time has elapsed. Thus, according to one illustrative, non-limiting example an anticoagulant material may be applied, at least partially, to one or more of the opening 14, skin interface member 16, passageway 22, or any other components or members with which the body fluid comes into contact. Examples of suitable anticoagulant materials may include, but are not limited to, aspirin, heparin and Coumadin®. According to a further alternative embodiment, and additional agent or material may be applied to either the opening 14, skin interface member 16, passageway 22, or other components are members with which the body fluid comes into contact that improves the flow of body fluid. Such additional agents or materials include, for example, Silwet®. According to additional alternative embodiment, one or more of the above-mentioned parts or components of the arrangement 10 or device 11 can be coated with a combination of these two types of materials. According to one illustrative, non-limiting example, one or more of the above-mentioned parts or components are coated with a solution having a composition such as: 49.4 ml of sterile water+49.4 ml of sterile isopropyl alcohol+0.8 ml of Silwet™ L7600+0.46 grams of low molecular weight heparin.

Devices, arrangements and techniques according to additional optional embodiments are illustrated in FIGS. 4-10. It should be understood that the devices, arrangements and techniques of these additional alternative embodiments can be utilized in connection with the practice of any of the foregoing techniques or methods of the present invention. However, the present invention is not necessarily so limited. The devices, arrangements and techniques of these additional alternative embodiments can be utilized in connection with the practice of additional techniques or methods not described herein. Similarly, the devices, arrangements and techniques of the additional alternative embodiments of FIGS. 4-10 may possess any or all of the features and/or functionality of the previously described embodiments (e.g., FIGS. 2-3). However, these additional alternative embodiments are not so limited. The techniques, devices and arrangements depicted in FIGS. 4-10 may be successfully utilized in connection with other devices or arrangements not previously described herein. When the additional alternative embodiments depicted in FIGS. 4-10 possess features which are common to the previously described embodiments (e.g., FIGS. 2-3), the same reference numerals have been utilized to identify such common features. In the interest of conciseness, such common features may not be fully described in the following description of these additional alternative embodiments. The description of these common features contained in the embodiments depicted in FIGS. 4-10 are incorporated herein by reference to their previous description in connection with the previously-described embodiments.

Figure 4:
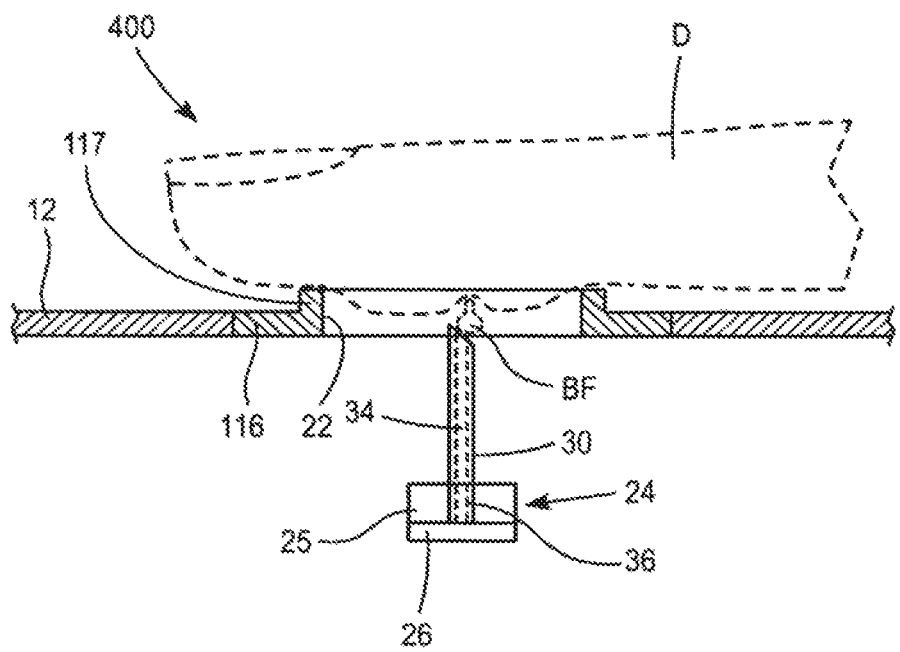
FIG. 4 is a partial sectional view of an alternative embodiment of the present invention.

FIG. 4 illustrates an arrangement 400 formed according to an optional alternative embodiment of the present invention. The arrangement 400 includes a slightly modified skin interface member 116. The skin interface member can be formed from any suitable material, such as an elastomer, silicone rubber, plastic, or combination of different materials. The skin interface member 116 may further comprise an optional rim-like formation 117. The rim-like formation 117 may provide the advantage of creating a ring of pressure along the surface of the skin applied thereto thereby facilitating the body fluid BF sample collection procedure. Regardless of whether the optional rim-like formation 117 is present, as illustrated in broken-line in FIG. 4, the skin has a tendency to sag and project downwardly into the opening our passageway 22 defined by the skin interface member 116. This sagging effect can be even more pronounced when, for example, a vacuum catalyst is applied during the course of the body fluid BF sample collection effort.

FIG. 4 depicts an attempt to apply a sample of body fluid BF to an analyte quantification member 24. The analyte quantification member 24 includes a hub 25, with a reagent pad 26 attached thereto. The skin-penetration member 30 is provided in the form of a hollow needle having an inner lumen 34. The inner lumen 34 is in fluid communication with the assay at 26. This fluid communication can be provided through a number of possible arrangements. Thus, an end of the skin-penetration member 30 can be mounted all the way through the hub so that it directly communicates with the reagent pad 26. Alternatively, an end of the skin-penetration member 30 can be mounted to the hub in a manner such that the end is based from the reagent pad 26, in which case the hub 25 may optionally be provided with a separate passage 36 communicating with the end of the skin-penetration member 30 and be at reagent pad 26.

As further illustrated in FIG. 4, and according to one alternative embodiment, once additional measures have been taken in order to obtain an additional volume of body fluid, possibly in response to an indication from a device or arrangement that an initial attempt failed to produce an adequate sample volume, the user places the skin into contact with the skin interface member 116 such that the wound created by the initial attempt is approximately located in the center of the opening defined by the skin penetration member 116. When so located, the arrangement 400 is constructed such that the end of the skin-penetration member having an opening defined by the end of the inner lumen 34 will be in close proximity to the wound, and the additional volume of body fluid BF being expressed therefrom can be brought into communication with said opening. Since the inner lumen 34 is in fluid communication with the analyte quantification member 24, including the reagent pad 26, the body fluid BF is transported to the reagent pad 26 via gravity, capillary effects, or combination of the two. As previously described herein, steps can then be taken to determine if the reapplication of body fluid BF has been successful in order to provide an adequate sample volume to conduct an assay.

Figure 5:
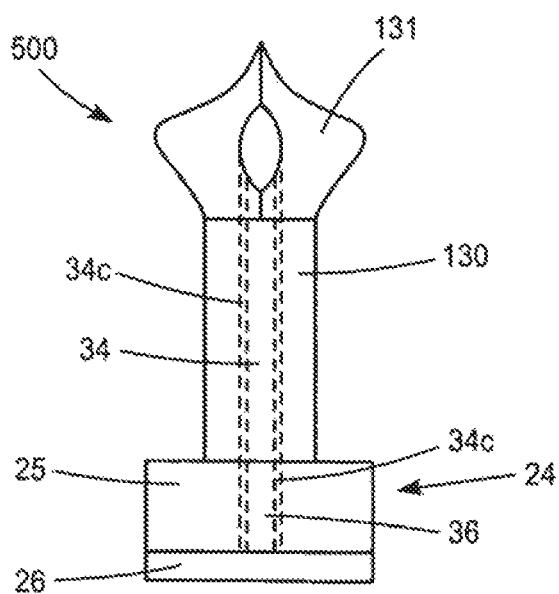
FIG. 5 is a side view of an additional embodiment of the present invention.

FIG. 5 illustrates an arrangement 500 comprising a modified skin penetration member construction 130 designed to facilitate receiving body fluid BF applied thereto. As illustrated therein, the skin penetration member 130 is provided with an end 131 which is provided with a geometry which has been optimized to present a surface which is more likely to be successful in receiving a sample of body fluid BF applied thereto. The end 131 is not limited to the illustrated configuration, but instead may have any suitable geometric shape that increases the likelihood of capturing a drop of body fluid applied thereto. The skin penetration member 130 can be formed from any suitable material, such as those materials previously described herein in connection with the skin penetration member 30 of the previously described embodiments. Moreover, the skin penetration member 130 can have an inner lumen 34 provided with an optional body fluid BF flow enhancing feature 34c. The flow enhancing feature 34c can comprise a surface texturing or coating. When the flow enhancing feature 34c comprises a coating, it may optionally be in the form of an anticoagulant substance, such as those anticoagulant substances previously described herein. When the analyte quantification member 24 comprises a hub 25, the hub 25 can be provided with a separate passage 36 for fluid communication between the inner lumen 34 and the reagent pad 26. The passage 36 and a hub 25 may also comprise a body fluid BF flow enhancing feature 34c.

Figure 6:
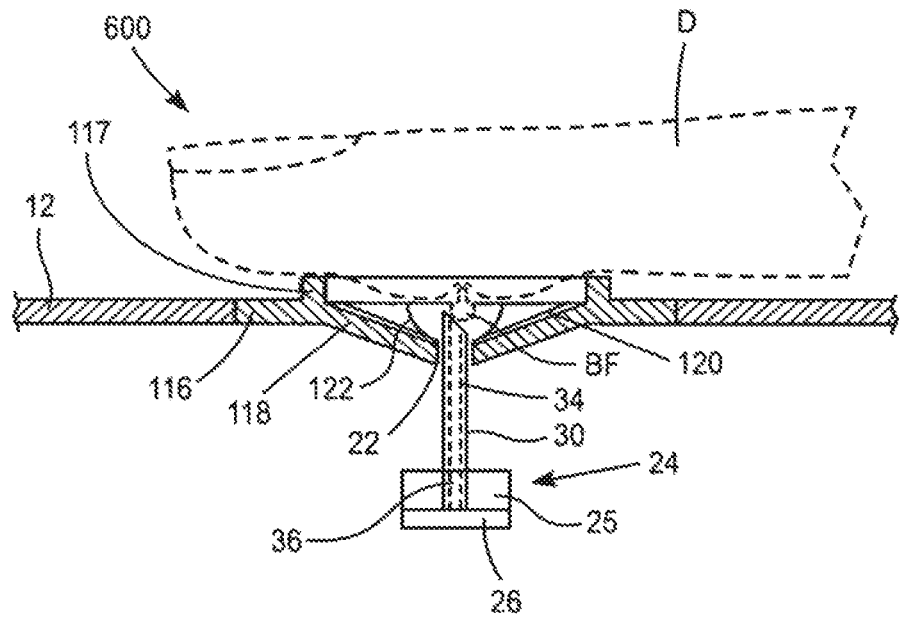
FIG. 6 is a partial sectional view of a further embodiment of the present invention.

An arrangement 600 constructed according to a further alternative embodiment is depicted in FIG. 6. As illustrated therein, the skin interface member 116 is provided with a guide element 118 which is configured to promote the flow of body fluid in a desired direction, i.e. toward an open end of a hollow skin penetration member 30 defined by the end of an inner lumen 34. The guide element 118 can be formed from the same material as the rest of the skin interface member 116. Alternatively, the guide element 118 can be formed from a different material than at least part of the remainder of the skin interface member 116. Thus, for example, the guide element 118 can be formed from a polymer material which is softer and/or more flexible than the remainder of the skin interface member 116, or vice versa. The guide element 118 can be formed from, or coated with, a high visibility material thus facilitating application of a drop of body fluid BF thereto. For example, the material or coating can comprise a bright color, reflective substance, and/or fluorescent substance. Alternatively, or in addition thereto, and associated device or arrangement can include a source of light that illuminates the guide element 118. The guide element 118 can comprise an integral part of the skin interface member 116. Alternatively, the guide element 118 can comprise a separate part or component which is either permanently or really simply attached to a remaining portion of the skin interface member 116. The guide element 118 can have any suitable geometric configuration or shape. Thus, according to certain nonlimiting examples, the guide element 118 can have a conical, frustoconical, or concave dome-like shape. At least the guide element 118 of the skin interface number 116 may optionally be provided with one or more body fluid flow-enhancing features. Therefore, at least a portion of the guide element 118 can be provided with a suitable coating 120 that promotes the flow of body fluid BF in a desired direction, toward a desired location. Coating 120 can comprise a hydrophilic coating, a hydrophobic coating, an anticoagulant coating, or combinations thereof. Alternatively, or in addition thereto, the guide element 118 may comprise a surface texturing, such as one or more capillary grooves 122 that also serve to promote the flow of body fluid in a desired direction, toward a desired location. As illustrated in FIG. 6, the coating 120 and grooves 122 can be utilized in combination with one another. Alternatively, the guide element 118 may comprise either a coating 120 or grooves 122 alone. As evident from the arrangement 600 depicted in FIG. 6, the provision of the guide element 118 is beneficial in that it permits a user some latitude in terms of how precisely the wound needs to be located relative to the position of the skin penetration member 30. The guide element 118 is configured such that if the body fluid BF is introduced onto any portion thereof, its flow is directed toward the end of the lumen 34 of the skin penetration member 30. It should be understood that the presence of a hollow needle type skin penetration member 30 is optional. Thus, for example, the arrangement 600 may be configured such that the guide element 118 directs the flow of body fluid BF directly to an analyte quantification member in fluid flow communications therewith. According to a further example, the guide element 118 can direct the flow of body fluid BF to another member or element, such as a hollow tube or similar fluid conveying or receiving structure.

Figure 7:
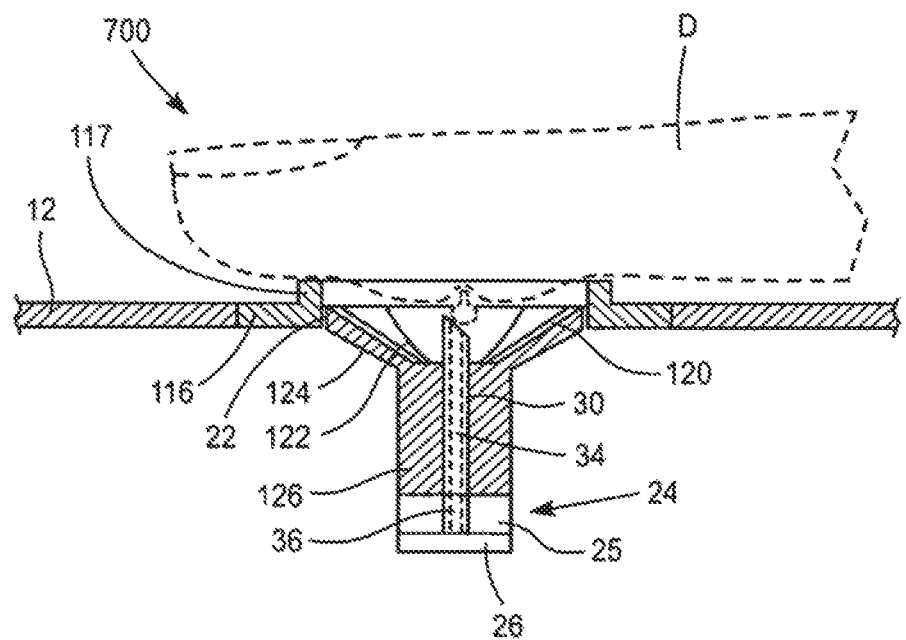
FIG. 7 is a partial sectional view of still another embodiment of the present invention.

FIG. 7 illustrates a further alternative arrangement 700 formed according to a further optional embodiment of the present invention. The arrangement 700 is similar to the previously described arrangement 600, except that a guide element 124 is associated with a skin penetration member 30. The guide element 124 can have the same construction, functionality and features as the guide element 118 described above. The guide element 124 can be associated with the skin penetration member 30 in any suitable fashion. According to the illustrated example, the guide element 124 is associated with the skin penetration member 30 via a collar-like portion 126, which surrounds at least a portion of the outer periphery of the skin penetration member 30. The guide element 124 can be integrally formed with the collar-like portion 126. Alternatively, the guide element 124 can be separately formed and attached in a permanent or releasable manner to the collar-like portion 126. When the analyte quantification member 24 includes a hub 25, the collar-like portion 126 can be connected to the hub 25 in any suitable manner, such as adhesively secured thereto. Alternatively, the collar-like portion 126 and the hub 25 can be integrally formed together as a single piece of the same material, or co-molded together to form a unitary structure. The guide element 124 of the arrangement 700 may perform an additional function, namely, act as a stop or limit for the depth of penetration of the skin penetration member 30 into the skin at the site of the wound. As previously described herein, the skin penetration member 30 can be actuated or driven into the surface of the skin located within the passage 22 of the skin interface member 16, thereby creating the wound. As illustrated in FIG. 7, the guide element 124 projects outwardly and upwardly relative to the skin penetration member 30. Thus, the uppermost surface of the guide element 124 can be configured and dimensioned such that it makes a desired degree of contact with the skin of a user. This contact can serve to limit the depth by which the skin penetration member may extend into the surface of the skin of the user. As described above in connection with the arrangement 600, it should be understood that the presence of a hollow needle type skin penetration member 30 is optional. Thus, for example, the arrangement 700 may be configured such that the guide element 124 directs the flow of body fluid BF directly to an analyte quantification member in fluid flow communications therewith. According to a further example, the guide element 124 can direct the flow of body fluid BF to another member or element, such as a hollow tube or similar fluid conveying or receiving structure.

Figure 8:
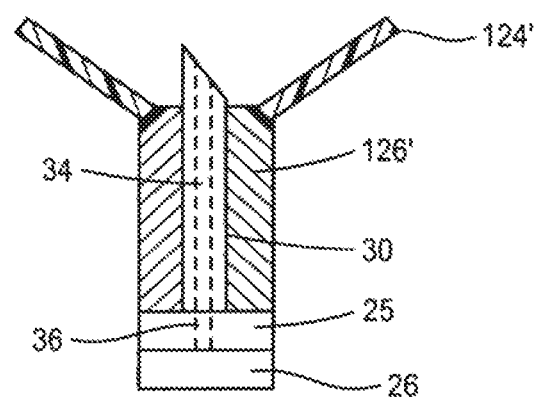
FIG. 8 is a partial sectional view of an arrangement formed according to a further aspect of the present invention

FIG. 8 illustrates an alternatively constructed skin penetration member/guide element construction. As illustrated therein, the guide element 124' and the collar-like portion 126' can be formed from separate materials having distinct properties. The guide element 124' and the collar-like portion 126' may be separately formed and permanently or releasable joined together, or co-molded together to form a unitary structure. Thus, for example, the guide element 124' can be formed from a softer or more flexible material than the collar-like portion 126'. This construction may have the benefit of providing a more compliant guide element 124' for easier interfacing with the user, while the more rigid collar-like portion 126' provides for accurate location which is not easily misaligned.

Figure 9:
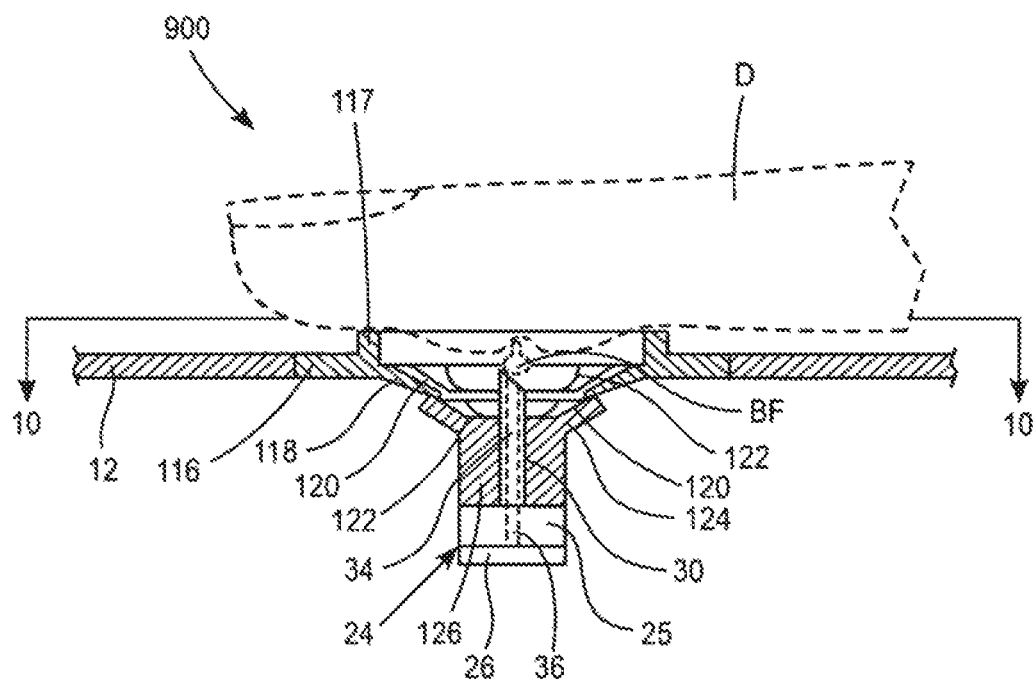
FIG. 9 is a partial sectional view of an arrangement formed according to a further alternative embodiment of the present invention.

FIGS. 9-10 are directed to yet another alternative arrangement 900 formed according to certain optional aspects of the present invention. The arrangement 900 has a construction similar to that of previously described arrangements 700, 800; however, according to the arrangement 900, both the skin interface member 116 and the skin penetration member 30 have guide elements 118, 124 associated therewith, respectively. The guide elements 118, 124 can have the same features, construction and functionality of the previously described embodiments. As described above in connection with the previous arrangements, it should be understood that the presence of a hollow needle type skin penetration member 30 is optional. Thus, for example, the arrangement 900 may be configured such that the guide elements 118, 124 direct the flow of body fluid BF directly to an analyte quantification member in fluid flow communications therewith. According to a further example, the guide elements 118, 124 can direct the flow of body fluid BF to another member or element, such as a hollow tube or similar fluid conveying or receiving structure.

Numbers expressing quantities of ingredients, constituents, reaction conditions, and so forth used in this specification are to be understood as being modified in all instances by the term "about." Notwithstanding that the numerical ranges and parameters setting forth, the broad scope of the subject matter presented herein are approximations, the numerical values set forth are indicated as precisely as possible. Any numerical value, however, inherently contains certain errors necessarily resulting from the standard deviation found in their respective measurement techniques. None of the elements recited in the appended claims should be interpreted as invoking 35 U.S.C. § 112, ¶6, unless the term "means" is explicitly used.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

We claim:

1. A method of performing an assay to determine the presence or concentration of an analyte contained in a sample of body fluid, the method comprising:
    obtaining first body fluid sample from a wound with an analyte meter comprising at least one assay pad and a sensor associated therewith;
    detecting the absence of an adequate sample volume on the at least one assay pad during a first time period using the analyte meter; and
    upon detecting the absence of an adequate sample volume on the at least one assay pad, initiating a second time period and signaling the user to manually milk the wound and to introduce an additional body fluid sample to the analyte meter to increase the sample volume.

2. The method of claim 1 wherein detecting the absence of an adequate sample volume on the at least one assay pad comprises interrogating the assay pad with the sensor during the first time period.

3. The method of claim 2, further comprising detecting the absence of an adequate sample volume within the second time period and upon detecting the absence of an adequate sample volume within the second time period, signaling the user that the assay is being terminated.

4. The method of claim 2, further comprising detecting an adequate sample volume within the second time period and upon detecting an adequate sample volume during the second time period, continuing with the assay.

5. The method of claim 4, further comprising interrogating the assay pad subsequent to the second time period to ascertain the concentration of the analyte.

6. The method of claim 1, wherein the analyte comprises glucose and the body fluid comprises blood.

7. The method of claim 1, wherein the at least one assay pad containing a chemical reagent formulated to produce a color change upon reaction with the analyte.

8. The method of claim 1, wherein the analyte meter comprises a plurality of assay pads.

9. The method of claim 8, wherein the analyte meter comprises a removable cartridge containing the plurality of assay pads.

10. The method of claim 7, wherein the sensor comprises an optical sensor constructed to produce signals indicative of the color change.

11. The method of claim 1, wherein the second time period is less than 1 minute.

12. The method of claim 11, wherein the second time period is 45 seconds or less.

13. The method of claim 1, wherein the signaling comprises producing at least one of a visual signal and an audible signal.

14. The method of claim 1, wherein the analyte meter further comprises at least one skin-penetration member, the method further comprising: piercing the skin of a user with the least one skin-penetration member thereby creating the wound.

15. The method of claim 14, wherein the skin is pierced prior to detecting the absence of an adequate sample volume on the at least one assay pad during the first time period.

16. The method of claim 1 further comprising, subsequent to signaling the user to manually milk the wound and to introduce an additional body fluid sample fluid, applying a catalyst to the skin in the vicinity of the wound.

17. The method of claim 16, wherein the catalyst comprises a vacuum.

18. The method of claim 14, further comprising applying a catalyst to the skin of the user prior to, during, or subsequent to piercing the skin with the at least one skin-penetration member.

19. The method of claim 18, wherein the catalyst comprises a vacuum.

20. The method of claim 1, further comprising providing the analyte meter with an anticoagulant material on at least portions thereof that normally contact the body fluid sample.

21. A method of performing an assay to determine the presence or concentration of an analyte contained in a sample of body fluid, the method comprising:
    obtaining, via a skin-penetration member of an analyte meter, a first body fluid sample from a wound of a user;
    detecting, via a sensor of the analyte meter and during a first time period, an absence of an adequate sample volume on an assay pad of the analyte meter; and
    upon detecting the absence of the adequate sample volume on the assay pad of the analyte meter during the first time period, initiating a second time period and signaling the user to manually milk the wound and introduce additionally expressed body fluid sample to the analyte meter via the skin penetration member to increase sample volume obtained by the analyte meter.

22. The method of claim 21, wherein detecting the absence of the adequate sample volume on the assay pad comprises interrogating the assay pad with the sensor of the analyte meter during the first time period.

23. The method of claim 22, further comprising detecting an adequate sample volume within the second time period, and upon detecting the adequate sample volume during the second time period, continuing with the assay.

24. The method of claim 21, wherein the assay pad contains a chemical reagent formulated to produce a color change upon reaction with the analyte.

25. The method of claim 24, wherein the sensor of the analyte meter comprises an optical sensor constructed to produce signals indicative of the produced color change.

26. The method of claim 21, further comprising piercing skin of the user with the skin-penetration member, thereby creating the wound.

27. The method of claim 26, wherein the skin is pierced prior to detecting the absence of an adequate sample volume on the assay pad during the first time period.

28. The method of claim 26, further comprising applying a catalyst to the skin of the user prior to, during, or subsequent to piercing the skin of the user with the skin-penetration member.

* * * * *